United States Patent
Firth et al.

(10) Patent No.: US 9,481,627 B2
(45) Date of Patent: Nov. 1, 2016

(54) METHODS FOR SUPPRESSING ISOMERIZATION OF OLEFIN METATHESIS PRODUCTS

(71) Applicant: Elevance Renewable Sciences, Inc., Woodridge, IL (US)

(72) Inventors: Bruce E. Firth, Woodridge, IL (US); Sharon E. Kirk, Woodridge, IL (US)

(73) Assignee: Elevance Renewable Sciences, Inc., Woodridge, IL (US)

(*) Notice: Subject to any disclaimer, the term of this patent is extended or adjusted under 35 U.S.C. 154(b) by 0 days.

(21) Appl. No.: 14/840,679

(22) Filed: Aug. 31, 2015

(65) Prior Publication Data

US 2016/0090343 A1    Mar. 31, 2016

Related U.S. Application Data

(63) Continuation of application No. 13/335,517, filed on Dec. 22, 2011, now Pat. No. 9,133,416.

(51) Int. Cl.

| | |
|---|---|
| *C07C 51/31* | (2006.01) |
| *C07C 7/20* | (2006.01) |
| *C11B 1/10* | (2006.01) |
| *C11B 3/00* | (2006.01) |
| *C11C 3/10* | (2006.01) |

(Continued)

(52) U.S. Cl.
CPC .............. *C07C 51/313* (2013.01); *C07C 7/20* (2013.01); *C11B 1/10* (2013.01); *C11B 3/006* (2013.01); *C11C 3/10* (2013.01); *B01J 2231/54* (2013.01); *C07C 51/50* (2013.01); *C11B 5/00* (2013.01); *C11B 5/0007* (2013.01); *C11B 5/0014* (2013.01); *C11B 5/0028* (2013.01); *Y10S 502/52* (2013.01)

(58) Field of Classification Search
None
See application file for complete search history.

(56) References Cited

U.S. PATENT DOCUMENTS

| | | | |
|---|---|---|---|
| 3,139,460 A * | 6/1964 | Eisenmann | ............... C07C 7/20 585/3 |
| 3,150,205 A | 9/1964 | Krane et al. | |
| 3,351,566 A | 11/1967 | Taylor et al. | |

(Continued)

FOREIGN PATENT DOCUMENTS

| | | |
|---|---|---|
| EP | 0167201 B2 | 11/1995 |
| EP | 0168091 B2 | 4/2003 |

(Continued)

OTHER PUBLICATIONS

Ackman, R.G. et al., "Ozonolysis of Unsaturated Fatty Acids," *Can. J. Chem.*, vol. 39, 1961, pp. 1956-1963.

(Continued)

*Primary Examiner* — In Suk Bullock
*Assistant Examiner* — Ali Z Fadhel
(74) *Attorney, Agent, or Firm* — Robert S. Dailey

(57) ABSTRACT

A method for suppressing isomerization of an olefin metathesis product produced in a metathesis reaction includes adding an isomerization suppression agent to a mixture that includes the olefin metathesis product and residual metathesis catalyst from the metathesis reaction under conditions that are sufficient to passivate at least a portion of the residual metathesis catalyst. The isomerization suppression agent includes (i) a salt and/or an ester of a phosphorous oxo acid, and/or (ii) a derivative of the phosphorous oxo acid in which at least one P—H bond has been replaced by a P—C bond, and/or (iii) a salt and/or an ester of the derivative. Methods of refining natural oils are described.

12 Claims, 3 Drawing Sheets

(51) Int. Cl.
*C07C 51/50* (2006.01)
*C11B 5/00* (2006.01)

(56) References Cited

U.S. PATENT DOCUMENTS

| | | | |
|---|---|---|---|
| 4,210,771 A | 7/1980 | Holcombe | |
| 4,515,899 A * | 5/1985 | Click | B01J 27/285 502/209 |
| 4,596,878 A * | 6/1986 | Click | B01J 27/285 549/259 |
| 4,701,433 A * | 10/1987 | Edwards | B01J 23/002 502/162 |
| 4,810,803 A * | 3/1989 | Edwards | B01J 23/002 549/259 |
| 4,943,396 A | 7/1990 | Johnson | |
| 4,992,605 A | 2/1991 | Craig et al. | |
| 5,043,485 A | 8/1991 | Fleckenstein et al. | |
| 5,091,116 A | 2/1992 | Krishnamurthy et al. | |
| 5,095,169 A | 3/1992 | Skeels et al. | |
| 5,113,030 A | 5/1992 | Chen et al. | |
| 5,146,033 A | 9/1992 | Schrock et al. | |
| 5,191,145 A | 3/1993 | Allen et al. | |
| 5,262,076 A | 11/1993 | Ishida et al. | |
| 5,264,606 A | 11/1993 | Moloy et al. | |
| 5,298,271 A | 3/1994 | Takashina et al. | |
| 5,342,909 A | 8/1994 | Grubbs et al. | |
| 5,348,755 A | 9/1994 | Roy | |
| 5,374,751 A | 12/1994 | Cheng et al. | |
| 5,391,385 A | 2/1995 | Seybold | |
| 5,401,866 A | 3/1995 | Cheng et al. | |
| 5,414,184 A | 5/1995 | Wu et al. | |
| 5,432,083 A | 7/1995 | Copeland et al. | |
| 5,484,201 A | 1/1996 | Goolsbee | |
| 5,532,163 A | 7/1996 | Yagi et al. | |
| 5,560,950 A | 10/1996 | Conte et al. | |
| 5,596,111 A | 1/1997 | Sibi et al. | |
| 5,597,600 A | 1/1997 | Munson et al. | |
| 5,653,966 A | 8/1997 | Bertoli et al. | |
| 5,675,051 A | 10/1997 | Chauvin et al. | |
| 5,747,409 A | 5/1998 | Commereuc | |
| 5,824,354 A | 10/1998 | Ritter et al. | |
| 5,840,942 A | 11/1998 | Oude Alink | |
| 5,864,049 A | 1/1999 | Dos Santos et al. | |
| 5,880,298 A | 3/1999 | Hillion et al. | |
| 5,932,261 A | 8/1999 | Unnithan | |
| 5,939,572 A | 8/1999 | Sibi et al. | |
| 5,959,129 A | 9/1999 | van Dam et al. | |
| 5,972,057 A | 10/1999 | Hayafuji et al. | |
| 6,033,706 A | 3/2000 | Silkeberg et al. | |
| 6,075,158 A | 6/2000 | Hill | |
| 6,127,560 A | 10/2000 | Stidham et al. | |
| 6,129,945 A | 10/2000 | Awad et al. | |
| 6,162,480 A | 12/2000 | van Buuren et al. | |
| 6,172,248 B1 | 1/2001 | Copeland et al. | |
| 6,175,047 B1 | 1/2001 | Hori et al. | |
| 6,207,209 B1 | 3/2001 | Jirjis et al. | |
| 6,210,732 B1 | 4/2001 | Papanton | |
| 6,214,764 B1 | 4/2001 | Gillespie | |
| 6,215,019 B1 | 4/2001 | Pederson et al. | |
| 6,248,911 B1 | 6/2001 | Canessa et al. | |
| 6,251,460 B1 | 6/2001 | Ganguli et al. | |
| 6,265,495 B1 | 7/2001 | Hirata et al. | |
| 6,271,430 B2 | 8/2001 | Schwab et al. | |
| 6,284,852 B1 | 9/2001 | Lynn et al. | |
| 6,288,251 B1 | 9/2001 | Tsuto et al. | |
| 6,303,837 B1 | 10/2001 | Gürtler et al. | |
| 6,313,365 B1 | 11/2001 | Hori et al. | |
| 6,368,648 B1 | 4/2002 | Bertram et al. | |
| 6,376,581 B1 | 4/2002 | Tanaka et al. | |
| 6,376,690 B1 * | 4/2002 | Grubbs | C08G 61/08 556/136 |
| 6,388,038 B1 | 5/2002 | Hirata et al. | |
| 6,395,669 B1 | 5/2002 | Sartain et al. | |
| 6,409,778 B1 | 6/2002 | Auschra et al. | |
| 6,440,057 B1 | 8/2002 | Ergün et al. | |
| 6,492,564 B1 | 12/2002 | Wiese et al. | |
| 6,506,944 B1 | 1/2003 | Schwab et al. | |
| 6,552,139 B1 | 4/2003 | Herrmann et al. | |
| 6,552,208 B1 | 4/2003 | Alander et al. | |
| 6,583,236 B1 | 6/2003 | Giardello et al. | |
| 6,605,748 B2 | 8/2003 | Wagener et al. | |
| 6,638,551 B1 | 10/2003 | Levy et al. | |
| 6,646,172 B1 | 11/2003 | Schwab et al. | |
| 6,677,495 B1 | 1/2004 | Schwab et al. | |
| 6,696,597 B2 | 2/2004 | Pederson et al. | |
| 6,706,299 B2 | 3/2004 | Thengumpillil et al. | |
| 6,740,134 B2 | 5/2004 | Angelico et al. | |
| 6,761,869 B1 | 7/2004 | Virtanen | |
| 6,800,316 B1 | 10/2004 | Perrut et al. | |
| 6,833,149 B2 | 12/2004 | Jirjis et al. | |
| 6,846,772 B2 | 1/2005 | Lok et al. | |
| 6,852,900 B2 | 2/2005 | Wurziger et al. | |
| 6,900,347 B2 | 5/2005 | Paulson et al. | |
| 6,916,448 B2 | 7/2005 | Commereuc et al. | |
| 6,960,272 B1 | 11/2005 | Tokas et al. | |
| 6,962,729 B2 | 11/2005 | Tokas et al. | |
| 6,982,155 B1 | 1/2006 | Fukuda et al. | |
| 6,998,050 B2 | 2/2006 | Nakajoh et al. | |
| 7,025,851 B2 | 4/2006 | Caster et al. | |
| 7,045,100 B2 | 5/2006 | Ergün et al. | |
| 7,045,114 B2 | 5/2006 | Tonkovich et al. | |
| 7,060,316 B2 | 6/2006 | Sakai et al. | |
| 7,067,584 B2 | 6/2006 | Rink et al. | |
| 7,119,216 B2 | 10/2006 | Newman et al. | |
| 7,141,083 B2 | 11/2006 | Jordan | |
| 7,144,433 B2 | 12/2006 | Jordan | |
| 7,144,435 B2 | 12/2006 | Jordan | |
| 7,160,338 B2 | 1/2007 | Jordan | |
| 7,160,339 B2 | 1/2007 | Jordan | |
| 7,176,336 B2 | 2/2007 | Maughon et al. | |
| 7,220,289 B2 | 5/2007 | Jordan | |
| 7,276,616 B2 | 10/2007 | Dwyer et al. | |
| 7,320,809 B2 | 1/2008 | Friedman et al. | |
| 7,361,621 B2 | 4/2008 | Yang et al. | |
| 7,431,749 B2 | 10/2008 | Kim et al. | |
| 7,442,248 B2 | 10/2008 | Timmons | |
| 7,449,591 B2 | 11/2008 | Brenner et al. | |
| 7,452,515 B1 | 11/2008 | Lafleur et al. | |
| 7,507,846 B2 | 3/2009 | Pelly | |
| 7,507,854 B2 | 3/2009 | Lee et al. | |
| 7,563,915 B2 | 7/2009 | Matson et al. | |
| 7,576,227 B2 | 8/2009 | Lysenko et al. | |
| 7,585,990 B2 | 9/2009 | van Toor et al. | |
| 7,597,783 B2 | 10/2009 | Kruidenberg | |
| 7,598,407 B2 | 10/2009 | Kruidenberg | |
| 7,601,309 B2 | 10/2009 | Krupa et al. | |
| 7,612,221 B2 | 11/2009 | Haas et al. | |
| 7,626,047 B2 | 12/2009 | Nakayama et al. | |
| 7,626,048 B2 | 12/2009 | Soane et al. | |
| 7,645,807 B1 | 1/2010 | Goetsch et al. | |
| 7,652,145 B2 | 1/2010 | Herrmann et al. | |
| 7,652,156 B2 | 1/2010 | Hillion et al. | |
| 7,666,234 B2 | 2/2010 | Ghosh et al. | |
| 7,671,224 B2 | 3/2010 | Winde et al. | |
| 7,695,533 B2 | 4/2010 | Kovacs et al. | |
| 7,696,376 B2 | 4/2010 | Furuta | |
| 7,696,398 B2 | 4/2010 | Burdett et al. | |
| 7,718,833 B2 | 5/2010 | Potthast et al. | |
| 7,737,233 B2 | 6/2010 | Obrecht et al. | |
| 7,743,828 B2 | 6/2010 | Roddy et al. | |
| 7,745,652 B2 | 6/2010 | Lysenko et al. | |
| 7,750,172 B2 | 7/2010 | Grubbs et al. | |
| 7,790,651 B2 | 9/2010 | Lin et al. | |
| 7,806,945 B2 | 10/2010 | Jackam et al. | |
| 7,812,185 B2 | 10/2010 | Burdett et al. | |
| 7,812,187 B2 | 10/2010 | Kawashima et al. | |
| 7,838,711 B2 | 11/2010 | Herweck et al. | |
| 7,863,471 B2 | 1/2011 | Krause et al. | |
| 8,703,888 B2 | 4/2014 | Drozdzak et al. | |
| 2003/0023123 A1 | 1/2003 | Paulson et al. | |
| 2003/0135080 A1 | 7/2003 | Botha et al. | |
| 2004/0106512 A1 * | 6/2004 | Mackewitz | B01J 31/20 502/102 |
| 2005/0070750 A1 | 3/2005 | Newman et al. | |

(56) References Cited

U.S. PATENT DOCUMENTS

| | | |
|---|---|---|
| 2005/0203324 A1 | 9/2005 | Lee et al. |
| 2006/0042158 A1 | 3/2006 | Lee |
| 2006/0047176 A1 | 3/2006 | Gartside et al. |
| 2006/0069274 A1 | 3/2006 | Dias De Moraes E Silva et al. |
| 2006/0167326 A1 | 7/2006 | Burdett et al. |
| 2007/0011943 A1 | 1/2007 | Lin |
| 2007/0151146 A1 | 7/2007 | Lee et al. |
| 2007/0179302 A1 | 8/2007 | Olivier-Bourbigou et al. |
| 2007/0208206 A1 | 9/2007 | Obrecht et al. |
| 2007/0217965 A1 | 9/2007 | Johnson et al. |
| 2007/0225536 A1 | 9/2007 | Lutz |
| 2007/0227400 A1 | 10/2007 | Zullo et al. |
| 2007/0277430 A1 | 12/2007 | Jackman et al. |
| 2008/0047194 A1 | 2/2008 | Prawoto |
| 2008/0097114 A1 | 4/2008 | Bakshi |
| 2008/0103346 A1 | 5/2008 | Burdett et al. |
| 2008/0115407 A1 | 5/2008 | Hoffman |
| 2008/0119664 A1 | 5/2008 | Sinoncelli et al. |
| 2008/0202021 A1 | 8/2008 | Powell |
| 2008/0229654 A1 | 9/2008 | Bradin |
| 2008/0244962 A1 | 10/2008 | Abhari et al. |
| 2008/0282606 A1 | 11/2008 | Plaza et al. |
| 2008/0300434 A1 | 12/2008 | Cortright et al. |
| 2008/0306230 A1 | 12/2008 | Pan et al. |
| 2009/0038209 A1 | 2/2009 | Farid et al. |
| 2009/0048459 A1 | 2/2009 | Tupy et al. |
| 2009/0069516 A1 | 3/2009 | Obrecht et al. |
| 2009/0112007 A1 | 4/2009 | Lin et al. |
| 2009/0143544 A1 | 6/2009 | Lysenko et al. |
| 2009/0145022 A1 | 6/2009 | Ng et al. |
| 2009/0163731 A1 | 6/2009 | Martin et al. |
| 2009/0165366 A1 | 7/2009 | Jovanovic et al. |
| 2009/0178330 A1 | 7/2009 | Lebron Parejo et al. |
| 2009/0183420 A1 | 7/2009 | Cobb |
| 2009/0203860 A1 | 8/2009 | Bergbreiter et al. |
| 2009/0287004 A1 | 11/2009 | Bergman et al. |
| 2009/0306441 A1 | 12/2009 | Basset et al. |
| 2009/0307966 A1 | 12/2009 | Yan et al. |
| 2009/0324514 A1 | 12/2009 | Awad |
| 2009/0326295 A1 | 12/2009 | Krupa et al. |
| 2010/0010246 A1 | 1/2010 | Yan et al. |
| 2010/0018902 A1 | 1/2010 | Brownscombe et al. |
| 2010/0022789 A1 | 1/2010 | Mignani et al. |
| 2010/0037667 A1 | 2/2010 | Calderon et al. |
| 2010/0043280 A1 | 2/2010 | Morris |
| 2010/0087671 A1 | 4/2010 | Lemke |
| 2010/0093944 A1 | 4/2010 | Müller et al. |
| 2010/0094034 A1 | 4/2010 | Kaido et al. |
| 2010/0107474 A1 | 5/2010 | Talwar et al. |
| 2010/0113719 A1 | 5/2010 | Patton et al. |
| 2010/0121087 A1 | 5/2010 | Banavali et al. |
| 2010/0130769 A1 | 5/2010 | Banavali et al. |
| 2010/0132252 A1 | 6/2010 | Nakazono |
| 2010/0140136 A1 | 6/2010 | Spilker et al. |
| 2010/0160506 A1 | 6/2010 | Wu et al. |
| 2010/0163459 A1 | 7/2010 | Odueyungbo |
| 2010/0166620 A1 | 7/2010 | Gurski et al. |
| 2010/0167910 A1 | 7/2010 | Odueyungbo |
| 2010/0191008 A1 | 7/2010 | Olson |
| 2010/0212219 A1 | 8/2010 | Siochi et al. |
| 2010/0212220 A1 | 8/2010 | Tirmizi |
| 2010/0223842 A1 | 9/2010 | Thesz et al. |
| 2010/0228042 A1 | 9/2010 | Chun et al. |
| 2010/0234625 A1 | 9/2010 | Papadogianakis et al. |
| 2010/0236984 A1 | 9/2010 | Brookhart et al. |
| 2010/0242348 A1 | 9/2010 | Chen et al. |
| 2010/0243961 A1 | 9/2010 | Hilton et al. |
| 2010/0252485 A1 | 10/2010 | Soane et al. |
| 2010/0263263 A1 | 10/2010 | O'Rear |
| 2010/0264015 A1 | 10/2010 | Portnoff et al. |
| 2010/0305354 A1 | 12/2010 | DuBois |
| 2010/0307051 A1 | 12/2010 | Tremblay et al. |
| 2010/0331558 A1 | 12/2010 | Kao et al. |
| 2011/0015419 A1 | 1/2011 | Pendleton et al. |
| 2011/0113679 A1 | 5/2011 | Cohen et al. |
| 2011/0160472 A1 | 6/2011 | Lemke et al. |
| 2013/0085288 A1 | 4/2013 | Snead et al. |
| 2013/0237675 A1 | 9/2013 | Drozdzak et al. |

FOREIGN PATENT DOCUMENTS

| | | |
|---|---|---|
| EP | 1 728 844 A1 | 12/2006 |
| JP | 05-004938 A | 1/1993 |
| WO | WO 01/36368 A2 | 5/2001 |
| WO | WO 01/83097 A2 | 11/2001 |
| WO | WO 02/10114 A2 | 2/2002 |
| WO | WO 02/076920 A1 | 10/2002 |
| WO | WO 2004/037754 A2 | 5/2004 |
| WO | WO 2006/043281 A1 | 4/2006 |
| WO | WO 2006/052688 A2 | 5/2006 |
| WO | WO 2006/076364 A2 | 7/2006 |
| WO | WO 2007/027669 A1 | 3/2007 |
| WO | WO 2007/027955 A2 | 3/2007 |
| WO | WO 2007/092632 A2 | 8/2007 |
| WO | WO 2007/113530 A2 | 10/2007 |
| WO | WO 2008/048520 A1 | 4/2008 |
| WO | WO 2008/048522 A1 | 4/2008 |
| WO | WO 2008/058664 A1 | 5/2008 |
| WO | WO 2008/063322 A2 | 5/2008 |
| WO | WO 2008/104929 A1 | 9/2008 |
| WO | WO 2008/152371 A1 | 12/2008 |
| WO | WO 2009/007234 A1 | 1/2009 |
| WO | WO 2009/020665 A1 | 2/2009 |
| WO | WO 2009/020667 A1 | 2/2009 |
| WO | WO 2009/065229 A1 | 5/2009 |
| WO | WO 2009/089591 A1 | 7/2009 |
| WO | WO 2010/021740 A1 | 2/2010 |
| WO | WO 2010/051268 A1 | 5/2010 |
| WO | WO 2010/062958 A1 | 6/2010 |
| WO | WO 2010/074738 A1 | 7/2010 |
| WO | WO 2010/096549 A2 | 8/2010 |
| WO | WO 2010/097519 A2 | 9/2010 |
| WO | WO 2010/104844 A2 | 9/2010 |
| WO | WO 2010/124030 A1 | 10/2010 |
| WO | WO 2011/046872 A2 | 4/2011 |
| WO | WO 2012/129479 A2 | 9/2012 |

OTHER PUBLICATIONS

Bryan, Tom, "Adsorbing It All," *Biodiesel Magazine*, Mar. 2005, pp. 40-43.

Foglia, T.A., et al., "Oxidation of Unsaturated Fatty Acids With Ruthenium and Osmium Tetroxide," *J. Am. Oil Chemists' Soc.*, vol. 54, Nov. 1977, pp. 870A-872A.

Kram, Jerry W., "Cleaner and Clearer," *Biodiesel Magazine*, Jan. 2008, 4 pages.

Noureddini, H. et al., "Liquid-Phase Catalytic Oxidation of Unsaturated Fatty Acids," *Journal of American Oil Chemists' Society*, vol. 76, No. 3, 1999, pp. 305-312.

Oakley, Michael A., et al., "Practical Dihydroxylation and C-C Cleavage of Unsaturated Fatty Acids," *Journal of Molecular Catalysis A: Chemical*, vol. 150, 1999, pp. 105-111.

Patel, Jim et al., "High Conversion and Productive Catalyst Turnovers in Cross-Metathesis Reactions of Natural Oils With 2-Butene," *Green Chem.*, vol. 8, 2006, pp. 450-454.

Rüsch gen. Klaas, M., et al., "Transition-Metal Catalyzed Oxidative Cleavage of Unsaturated Fatty Acids," *Fat Sci. Technol.*, vol. 95(10), 1995, pp. 359-367.

Santacesaria, E., et al., "Oxidative Cleavage of the Double Bond of Monoenic Fatty Chains in Two Steps: A New Promising Route to Azelaic Acid and Other Industrial Products," *Ind. Eng. Chem. Res.*, vol. 39, 2000, pp. 2766-2771.

Santacesaria, E. et al., "Double Bond Oxidative Cleavage of Monoenic Fatty Chains," *Catalysis Today*, vol. 79-80, 2003, pp. 59-65.

Throckmorton, P.E. et al., "Pilot Run, Plant Design and Cost Analysis for Reductive Ozonolysis of Methyl Soyate," *Research and Development Laboratories*, 1967, p. 643.

Throckmorton, P.E. et al., "Reductive Ozonolysis of Soybean Oil: Laboratory Optimization of Process Variables," *Research and Development Laboratories*, p. 641.

(56) References Cited

OTHER PUBLICATIONS

Turnwald, S.E., et al., "Oleic Acid Oxidation Using Hydrogen Peroxide in Conjunction With Transition Metal Catalysis," *Journal of Materials Science Letters*, vol. 17, 1998, pp. 1305-1307.
International Search Report and Written Opinion of the International Searching Authority for International Application No. PCT/US2010/052174, dated Apr. 15, 2011, 9 pages.
International Search Report for International Application No. PCT/US2012/070550, dated Oct. 4, 2013, 2 pages.
Fee et al., "Phosphorus Compounds" in Kirk-Othmer Encyclopedia of Chemical Technology, J. Wiley & Sons, 2006, 17 pages.
Office Action issued in U.S. Appl. No. 13/335,466, mailed Oct. 21, 2014, 13 pages.
Ahn, Y. M.; Yang, K.; Georg, G. I. "A Convenient Method for the Efficient Removal of Ruthenium Byproducts Generated during Olefin Metathesis Reactions." Org. Lett., 2001, 3, 1411-1413.
Bourgeois, Damien et al., "The $Cl_2(PCy3)(IMes)Ru(=CHPh)$ catalyst: olefin metathesis versus olefin isomerization," Journal of Organic Metallic Chemistry, vol. 643-644, 2002, pp. 247-252.
Cho, J. H.; Kim, B. M. "An Efficient Method for Removal of Ruthenium Byproducts from Olefin Metathesis Reactions." Org. Lett., 2003, 5, 531-533.
Cotton, F. A.; Wilkinson, G. Advanced Inorganic Chemistry, Fifth Edition, New York: John Wiley & Sons, 1988, pp. 382-443.
Formentín, P.; Gimeno, N.; Steinke, J. H. G.; Vilar, R. "Reactivity of Grubbs' Catalysts with Urea- and Amide-Substituted Olefins. Metathesis and Isomerization." J. Org. Chem., 2005, 70, 8235-8238.
Galan, B. R.; Kalbarczyk, K. P.; Szczepankiewicz, S.; Keister, J. B.; Diver, Steven T. "A Rapid and Simple Cleanup Procedure for Metathesis Reactions." Org. Lett., 2007, 9, 1203-1206.
Gimeno, N.; Formentín, P.; Steinke, J. H. G.; Vilar, R. "Phenylphosphoric Acid as a New Additive to Inhibit Olefin Isomerization in Ruthenium-Catalyzed Metathesis Reactions." Eur. J. Org. Chem., 2007, 918-924.
Hong, S. H.; Sanders, D. P.; Lee, C. W.; Grubbs, R. H. "Prevention of Undesirable Isomerization During Olefin Metathesis." J. Am. Chem. Soc., 2005, 127, 17160-17161.
James, B. R.; Lorenzini, F. "Developments in the Chemistry of Tris(hydroxymethyl)phosphine." Coordination Chemistry Reviews, 2010, 254, 420-430.
Knight, D. W.; Morgan, I. R.; Proctor, A. J. "A Simple Oxidative Procedure for the Removal of Ruthenium Residues from Metathesis Reaction Products." Tetrahedron Letters, 2010, 51, 638-640.
Maynard, H. D.; Grubbs, R. H. "Purification Technique for the Removal of Ruthenium from Olefin Metathesis Reaction Products," Tetrahedron Letters, 1999, 40, 4137-4140.
McEleney, K.; Allen, D. P.; Holliday, A. E.; Cruciden, C. M. "Functionalized Mesoporous Silicates for the Removal of Ruthenium from Reaction Mixtures." Org. Lett., 2006, 8, 2663-2666.
Paquette, L. A.; Schloss, J. D.; Efremov, I.; Fahris, F.; Gallou, F.; Mendez-Andino, J.; Yang, J. "A Convenient Method for Removing All Highly-Colored Byproducts Generated during Olefin Metathesis Reactions." Org. Lett., 2000, 2, 1259-1261.
Pederson, R. L.; Fellows, I. M.; Ung, T. A.; Ishihara, H.; Hajela, S. P. "Applications of Olefin Cross Metathesis to Comniercial Products." Advanced Synthesis & Catalysis, 2002, 344, 728-735.
Wang, H.; Goodman, S. Ni; Dai, Q.; Stockdale, G. W.; Clark, W. M. "Development of a Robust Ring-Closing Metathesis Reaction in the Synthesis of SB-462795, a Cathepsin K Inhibitor." Organic Process Research & Development, 2008, 12, 226-234.
U.S. Appl. No. 12/672,652, filed Sep. 7, 2011 Entitled "Thermal Methods for Treating a Metathesis Feedstock".
U.S. Appl. No. 12/672,651, filed Sep. 7, 2011 Entitled "Chemical Methods for Treating a Metathesis Feedstock".
U.S. Appl. No. 13/335,466, entitled "Methods for Suppressing Isomerization of Olefin Metathesis Products" Filed Dec. 22, 2011.
U.S. Appl. No. 13/335,495, entitled "Methods for Suppressing Isomerization of Olefin Metathesis Products" Filed Dec. 22, 2011.
U.S. Appl. No. 13/335,538, entitled "Methods of Refining Natural Oils, and Methods of Producing Fuel Compositions" Filed Dec. 22, 2011.
U.S. Appl. No. 13/335,584, entitled "Methods of Refining Natural Oils, and Methods of Producing Fuel Compositions" Filed Dec. 22, 2011.
U.S. Appl. No. 13/335,601, entitled "Methods of Refining Natural Oils, and Methods of Producing Fuel Compositions" Filed Dec. 22, 2011.
International Search Report and Written Opinion of the International Searching Authority issued in PCT Patent Application No. PCT/US2013/063861, mailed Mar. 24, 2014, 12 pages.
Rybak et al., "Cross-metathesis of fatty acid derivatives with methyl acrylate: renewable raw materials for the chemical industry" Green Chem, 9, 2007, pp. 1356-1361.
Forman et al., "Improved cross-metathesis of acrylate esters catalyzed by $2^{nd}$ generation ruthenium carbine complexes" Journal of Organometallic Chemistry, 690, 2005, pp. 5863-5866.
Schrock, "High Oxidation State Multiple Metal-Carbon Bonds" Chem. Rev., 102, 2002, pp. 145-179.
Schrock et al., "Molybdenum and Tungsten Imido Alkylidene Complexes as Efficient Olefin-Metathesis Catalysts" Angew, Chem. Int. Ed., 42, 2003, pp. 4592-4633.
Schrock, "Recent Advances in High Oxidation State Mo and W Imido Alkylidene Chemistry" Chem. Rev., 109, 2009, pp. 3211-3226.
International Preliminary Report on Patentability issued in PCT Patent Application No. PCT/US2012/070255, mailed Jul. 3, 2014, 8 pages.
International Preliminary Report on Patentability issued in PCT Patent Application No. PCT/US2012/070275, mailed Jul. 3, 2014, 8 pages.
International Search Report and Written Opinion of the International Searching Authority issued in PCT Patent Application No. PCT/US2014/023530, mailed May 27, 2014, 11 pages.

\* cited by examiner

METHODS FOR SUPPRESSING ISOMERIZATION OF OLEFIN METATHESIS PRODUCTS

TECHNICAL FIELD

The present teachings relate generally to methods for suppressing the isomerization of olefins—particularly olefins produced in metathesis reactions.

BACKGROUND

The olefin metathesis reaction is a highly versatile and powerful technique for the synthetic preparation of alkenes. Transition metal carbene complexes—particularly those incorporating ruthenium—are popular catalysts for metathesis. However, the yield of certain desired metathesis products can be significantly reduced by double bond isomerization. This is typically the result of residual metathesis catalyst and/or its byproducts being present in the reaction mixture. This problem becomes particularly acute if the metathesis mixture is heated and/or distilled in the presence of residual catalyst.

In view of this problem, it is oftentimes necessary to remove residual metathesis catalyst from an olefinic metathesis product (or otherwise passivate the residual catalyst) prior to subjecting the olefinic metathesis product to further chemical reactions and/or processing. One approach, as described in U.S. Pat. No. 6,215,019 B1, has been to add tris(hydroxymethyl) phosphine (THMP) to the reaction mixture as an isomerization inhibitor. Unfortunately, the commercial availability and pricing of THMP are not viable on an industrial scale. Moreover, although THMP can be prepared from precursor salts, such as tetrakis(hydroxymethyl) phosphonium sulfate (THPS) or tetrakis(hydroxymethyl) phosphonium chloride (TKC), the conversion involves generation of formaldehyde—a known human carcinogen—as a byproduct. In addition, if pH is not strictly controlled during the formation of THMP (e.g., if conditions become too basic), explosive hydrogen gas has been known to form.

An isomerization suppression agent that efficiently passivates residual metathesis catalyst present in admixture with olefinic metathesis product, and which is readily available on a commercial scale but does not produce carcinogenic by-products and/or involve the formation of explosive hydrogen gas is needed.

SUMMARY

The scope of the present invention is defined solely by the appended claims, and is not affected to any degree by the statements within this summary.

By way of introduction, a first method for suppressing isomerization of an olefin metathesis product produced in a metathesis reaction includes adding an isomerization suppression agent to a mixture that includes the olefin metathesis product and residual metathesis catalyst from the metathesis reaction under conditions that are sufficient to passivate at least a portion of the residual metathesis catalyst. The isomerization suppression agent includes (i) a salt and/or a substantially water-insoluble ester of a phosphorous oxo acid, and/or (ii) a derivative of the phosphorous oxo acid in which at least one P—H bond has been replaced by a P—C bond, and/or (iii) a salt and/or an ester of the derivative.

A second method for suppressing isomerization of an olefin metathesis product produced in a metathesis reaction includes: (a) adding an isomerization suppression agent to a mixture that includes the olefin metathesis product and residual metathesis catalyst from the metathesis reaction under conditions that are sufficient to passivate at least a portion of the residual metathesis catalyst; and (b) processing the mixture to provide a fraction that comprises the olefin metathesis product and/or a derivative thereof, wherein the isomerization suppression agent is not removed from the mixture prior to the processing. The isomerization suppression agent includes (i) a salt and/or an ester of a phosphorous oxo acid, and/or (ii) a derivative of the phosphorous oxo acid in which at least one P—H bond has been replaced by a P—C bond, and/or (iii) a salt and/or an ester of the derivative.

DETAILED DESCRIPTION

Figure 1:
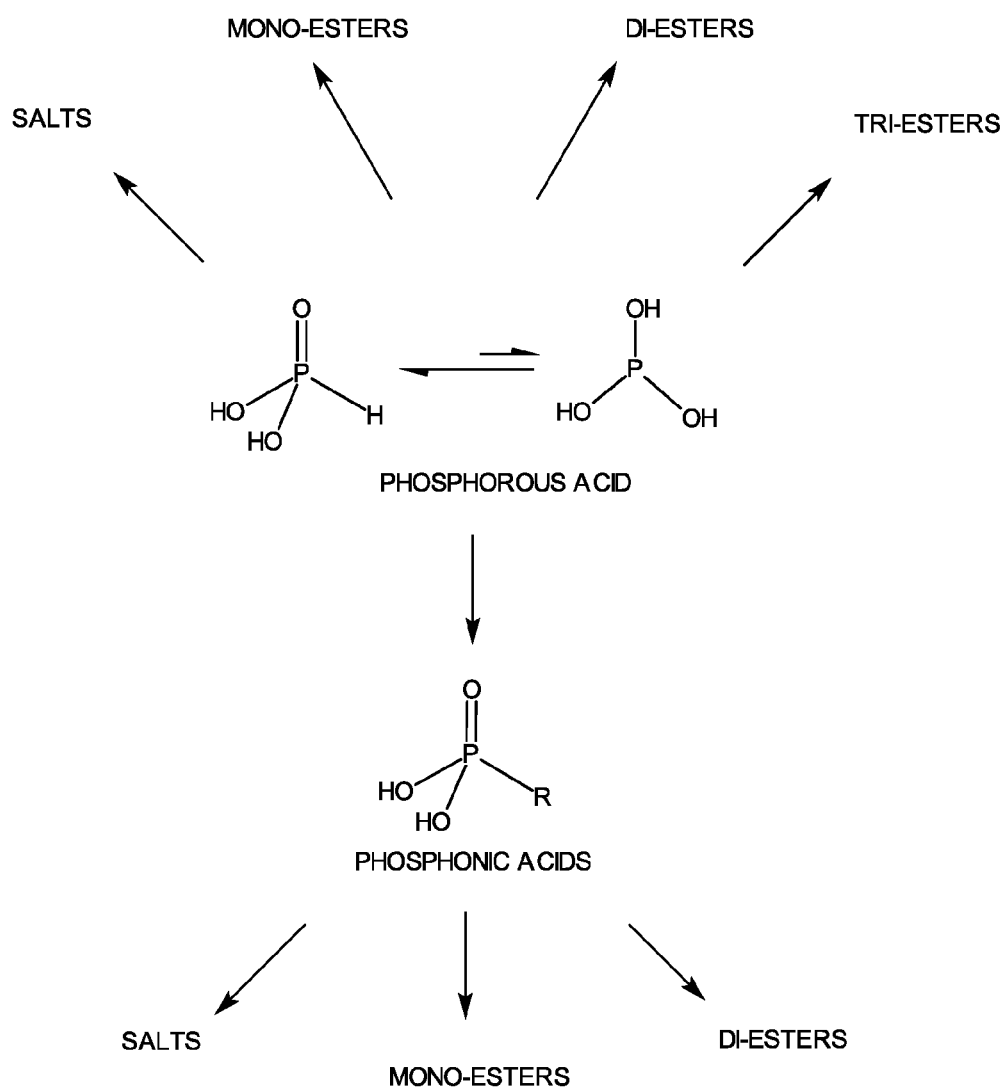
FIG. 1 shows representative phosphorous acid derivatives for use in accordance with the present teachings.

An effective methodology for suppressing the isomerization of olefin metathesis products—which is suitable for application on a large-scale, does not involve the generation of carcinogenic byproducts, such as formaldehyde, and is not susceptible to the generation of explosive gas, such as hydrogen—has been discovered and is described herein. In some embodiments, the inventive methodology utilizes (i) a salt and/or an ester of a phosphorous oxo acid, and/or (ii) a derivative of the phosphorous oxo acid in which at least one P—H bond has been replaced by a P—C bond, and/or (iii) a salt and/or an ester of the derivative. In some embodiments, the inventive methodology facilitates preservation of the original location of a carbon-carbon double bond created during a metathesis reaction, thereby facilitating subsequent processing of metathesized product and preserving product integrity.

In some embodiments of the inventive methodology, the mixture comprising the olefin metathesis product can be subjected to further processing—which, in some embodiments, optionally involves heating (e.g., distillation, transesterification, and/or the like)—in order to separate off and/or derivatize an olefin metathesis product. In some embodiments, surprisingly and unexpectedly, the mixture can be subjected to such processing directly and without first requiring removal of the isomerization suppression agent (e.g., via water extraction or the like). In some embodiments, surprisingly and unexpectedly, processing without first removing the isomerization suppression agent—even when heating is involved—does not substantially compromise the integrity of the olefin metathesis product and/or its derivatives. In some embodiments, a metathesized oil treated with an isomerization suppression agent in accordance with the present teachings can be separated (e.g., via distillation) into a triacylglyceride fraction (which, in some embodiments, can optionally be transesterified) and an olefinic fraction without first requiring the removal of the added isomerization suppression agent.

DEFINITIONS

Throughout this description and in the appended claims, the following definitions are to be understood:

The term "olefin" refers to a hydrocarbon compound containing at least one carbon-carbon double bond. As used herein, the term "olefin" encompasses hydrocarbons having more than one carbon-carbon double bond (e.g., di-olefins, tri-olefins, etc.). In some embodiments, the term "olefin" refers to a group of carbon-carbon double bond-containing compounds with different chain lengths. In some embodiments, the term "olefin" refers to poly-olefins, straight, branched, and/or cyclic olefins.

The term "suppressing" as used in reference to the isomerization of an olefin refers to an inhibitory effect on an olefin's susceptibility towards isomerization under a given set of conditions. It is to be understood that the term "suppressing" encompasses but does not necessarily imply 100% suppression (i.e., 0% isomerization).

The term "isomerization" as used in reference to an olefin metathesis product refers to the migration of a carbon-carbon double bond in the product to another location within the molecule (e.g., from a terminal position to an internal position and/or from an internal position to a terminal position and/or from a first internal position to a second internal position and/or from a first terminal position to a second terminal position, etc.).

The phrase "olefin metathesis product" refers to any product produced in a metathesis reaction that contains at least one carbon-carbon double bond. In some embodiments, the "olefin metathesis product" is an unfunctionalized hydrocarbon compound. In some embodiments, the phrase "olefin metathesis product" subsumes the term "olefin." In some embodiments, the "olefin metathesis product" is functionalized and contains one or a plurality of additional functional groups in addition to its at least one carbon-carbon double bond.

The term "functionalized" and the phrase "functional group" refer to the presence in a molecule of one or more heteroatoms at a terminal and/or an internal position, wherein the one or more heteroatoms is an atom other than carbon and hydrogen. In some embodiments, the heteroatom constitutes one atom of a polyatomic functional group with representative functional groups including but not limited to carboxylic acids, carboxylic esters, ketones, aldehydes, anhydrides, ether groups, cyano groups, nitro groups, sulfur-containing groups, phosphorous-containing groups, amides, imides, N-containing heterocycles, aromatic N-containing heterocycles, salts thereof, and the like, and combinations thereof.

The phrase "metathesis reaction" refers to a chemical reaction involving a single type of olefin or a plurality of different types of olefin, which is conducted in the presence of a metathesis catalyst, and which results in the formation of at least one new olefin product. The phrase "metathesis reaction" encompasses self-metathesis, cross-metathesis (aka co-metathesis; CM), ring-opening metathesis (ROM), ring-opening metathesis polymerizations (ROMP), ring-closing metathesis (RCM), acyclic diene metathesis (ADMET), and the like, and combinations thereof. In some embodiments, the phrase "metathesis reaction" refers to a chemical reaction involving a natural oil feedstock.

The phrase "phosphorous oxo acid" refers to a molecule that comprises a P—OH moiety in which the hydrogen atom is ionizable.

The phrase "higher acid" as used in reference to a phosphorous oxo acid refers to an acid in which phosphorous is in an oxidation state of +5.

The phrase "lower acid" as used in reference to a phosphorous oxo acid refers to an acid in which phosphorous is in an oxidation state below +5 (e.g., $P^{III}$).

The phrase "ester of a phosphorous oxo acid" refers to a molecule that comprises a P—OR bond, wherein R denotes any substituted or unsubstituted alkyl or aryl group.

The phrase "substantially water-insoluble" as used in reference to an ester of a phosphorous oxo acid refers to a molecule that partitions into an organic phase in preference to an aqueous phase. It is to be understood that the phrase "substantially water-insoluble" encompasses but does not necessarily imply 0% aqueous solubility.

The phrases "natural oil," "natural oil feedstock," and the like refer to oils derived from plant or animal sources. As used herein, these phrases encompass natural oil derivatives as well, unless otherwise indicated.

The term "derivative" as used in reference to a substrate (e.g., a "functionalized derivative" of a carboxylic acid, such as 9-decenoic acid, etc.) refers to compounds and/or mixture of compounds derived from the substrate by any one or combination of methods known in the art, including but not limited to saponification, transesterification, esterification, amidification, amination, imide preparation, hydrogenation (partial or full), isomerization, oxidation, reduction, and the like, and combinations thereof.

The phrase "natural oil derivatives" refers to compounds and/or mixture of compounds derived from a natural oil using any one or combination of methods known in the art, including but not limited to saponification, transesterification, esterification, amidification, amination, hydrogenation (partial or full), isomerization, oxidation, reduction, and the like, and combinations thereof.

The phrase "low-molecular-weight olefin" refers to any straight, branched or cyclic olefin in the $C_2$ to $C_{30}$ range and/or any combination of such olefins. The phrase "low-molecular-weight olefin" encompasses polyolefins including but not limited to dienes, trienes, and the like. In some embodiments, the low-molecular-weight olefin is functionalized.

The term "ester" as used in reference to olefin metathesis products and/or derivatives thereof refers to compounds having a general formula R—COO—R', wherein R and R' denote any substituted or unsubstituted alkyl or aryl group. In some embodiments, the term "ester" refers to a group of compounds having a general formula as described above, wherein the compounds have different chain lengths.

The phrase "residual metathesis catalyst" refers to a catalytic material left over from a metathesis reaction that is capable of participating in, catalyzing and/or otherwise promoting or facilitating the isomerization of a carbon-carbon double bond although it may or may not still be capable of catalyzing a metathesis reaction. As used herein, the phrase "residual metathesis catalyst" encompasses wholly unreacted metathesis catalyst, partially reacted metathesis catalyst, and all manner of chemical entities derived from a metathesis catalyst over the course of a metathesis reaction, including but not limited to all manner of active or inactive intermediates (e.g., carbenes, metallocycles, etc.), degradation and/or decomposition products (e.g., metal hydrides, ligand fragments, etc.), metals, metal salts, metal complexes, and the like, and combinations thereof.

The term "passivate" as used in reference to residual metathesis catalyst refers to any reduction in the activity of the residual metathesis catalyst vis-à-vis its ability and/or tendency to catalyze and/or otherwise participate in (e.g., via a stoichiometric chemical reaction, sequestration or the like) the isomerization of a carbon-carbon double bond. It is to be understood that the term "passivate" encompasses but does not necessarily imply complete deactivation of residual metathesis catalyst towards isomerization of a carbon-carbon double bond.

The phrase "conditions sufficient to passivate" as used in reference to the conditions under which an isomerization suppression agent is added to a mixture comprising olefin metathesis product and residual metathesis catalyst refers to a variable combination of experimental parameters, which together result in the passivation of at least a portion of residual metathesis catalyst. The selection of these individual parameters lies well within the skill of the ordinary artisan in view of the guiding principles outlined herein, and will vary according to the target reduction in degree of isomerization that is being sought for a particular application. As used herein, the phrase "conditions sufficient to passivate" encompasses experimental parameters including but not limited to concentrations of reagents, the type of mixing and/or stirring provided (e.g., high-shear, low-intensity, etc.), reaction temperature, residence time, reaction pressure, reaction atmosphere (e.g., exposure to atmosphere vs. an inert gas, etc.), and the like, and combinations thereof.

The phrase "degree of isomerization" as used in relation to an olefin metathesis product refers to an amount to which a carbon-carbon double bond in the olefin metathesis product undergoes migration from its original position to a subsequent position (e.g., the degree to which an initially formed olefin metathesis product is converted into one or more non-identical isomers thereof). In some embodiments, the "degree of isomerization" refers to the degree to which an initially formed α-olefin metathesis product is converted into one or more internal isomers thereof under a given set of conditions (e.g., the amount of terminal-to-internal migration). In some embodiments, the "degree of isomerization" refers to the degree to which an olefin metathesis product containing an internal carbon-carbon double bond is converted into an α-olefin under a given set of conditions (e.g., the amount of internal-to-terminal migration). In some embodiments, the "degree of isomerization" refers to the degree to which an olefin metathesis product containing an internal carbon-carbon double bond is converted into one or more additional and non-identical internal isomers thereof under a given set of conditions (e.g., the amount of internal-to-internal migration). In some embodiments, the "degree of isomerization" refers to the degree to which an initially formed α-olefin metathesis product is converted into a different α-olefin under a given set of conditions (e.g., the amount of terminal-to-terminal migration). In some embodiments, the "degree of isomerization" refers to any combination of the amount of terminal-to-internal migration, the amount of internal-to-terminal migration, the amount of internal-to-internal migration, and/or the amount of terminal-to-terminal migration.

The term "attached" as used in reference to a solid support and an isomerization suppression agent is to be understood broadly and without limitation to encompass a range of associative-type forces, including but not limited to covalent bonds, ionic bonds, physical and/or electrostatic attractive forces (e.g., hydrogen bonds, Van der Waals forces, etc.), and the like, and combinations thereof.

By way of general background, as mentioned above, the presence of residual metathesis catalyst during heating and/or distillation of an olefin metathesis product can result in the isomerization of a carbon-carbon double bond in the product, such that one or more isomers of the original olefin metathesis product are formed. Such isomerization is generally undesirable when end-group functionalization within the product molecule is the goal. In addition, such isomerization is generally undesirable when it leads to a mixture of products and the goal is a well-defined product in high yield and in high purity. Labile olefins and/or olefins that are not as thermodynamically stable as other isomers readily accessible through isomerization are particularly—though by no means exclusively—susceptible to isomerization (e.g., terminal olefins, vinyl olefins, vinylidene olefins, and the like).

By way of example, although methyl 9-decenoate is an expected product of the cross-metathesis between methyl oleate and the α-olefin 1-butene, it is found in practice that some isomerization of the 9-substituted olefin to one or more internal olefins (e.g., migration of the double bond to the 7- and/or 8-positions) can occur when the cross metathesis product is heated prior to removal and/or pacification of residual metathesis catalyst. To assess the magnitude of the isomerization, the cross-metathesized material obtained from the cross-metathesis between methyl oleate and 1-butene was subjected to typical oil refining conditions, such as exposure to high temperatures (e.g., about 250° C.). In the absence of any isomerization suppression agent, the degree of isomerization of methyl 9-decenoate to internal isomers under typical conditions was observed to be about 25%. It is to be understood, however, that this degree of isomerization is meant solely to be illustrative and that it can vary depending on the particular substrate and conditions.

However, by adding, for example, an ester of a phosphorous oxo acid as an isomerization suppression agent—particularly though not exclusively a phosphite ester (which, in some embodiments, has a molecular weight sufficiently high that the phosphite ester exhibits thermal stability), and particularly though not exclusively in an excess molar amounts relative to residual metathesis catalyst—the present inventors found that the degree of isomerization can be greatly reduced. Moreover, many esters of phosphorous oxo acids (e.g., various high molecular weight phosphite esters that are used as secondary antioxidants during high temperature polymer processes, including but not limited to the extrusion of polyolefins at temperatures above about 250° C.) are available in commercial quantities and are not subject to the same carcinogenicity and explosion concerns that are associated with THMP production.

It is to be understood that elements and features of the various representative embodiments described below may be combined in different ways to produce new embodiments that likewise fall within the scope of the present teachings.

By way of general introduction, in some embodiments, a method in accordance with the present teachings for suppressing isomerization of an olefin metathesis product produced in a metathesis reaction comprises adding an isomerization suppression agent to a mixture that comprises the olefin metathesis product and residual metathesis catalyst from the metathesis reaction. The isomerization suppression agent is added under conditions sufficient to passivate at least a portion of the residual metathesis catalyst, and is selected from the group consisting of (i) a salt and/or an ester of a phosphorous oxo acid, (ii) a derivative of the phosphorous oxo acid in which at least one P—H bond has been replaced by a P—C bond, (iii) a salt and/or an ester of the derivative, and (iv) combinations thereof. In some embodiments, the ester of the phosphorous oxo acid is substantially water-insoluble.

As described above, in some embodiments—particularly though not exclusively embodiments in which the isomerization suppression agent comprises a phosphite ester having a sufficiently high molecular weight and exhibiting a desired degree of thermal stability—the mixture comprising the olefin metathesis product can be subjected directly to further processing in the presence of the isomerization suppression agent. In other words, in some embodiments, it may not be possible, necessary, and/or desirable to remove the isomerization suppression agent via extraction with a polar solvent (e.g., water) prior to further processing, including but not limited to processing that involves heating. In some embodiments, one such isomerization suppression agent comprises a substantially water-insoluble ester of a phosphorous oxo acid which, in some embodiments, may not partition to a significant degree in a polar solvent.

It is to be understood that under a give set of biphasic conditions, a "substantially water-insoluble" ester of a phosphorous oxo acid may partition to some extent into the aqueous phase rather than the organic phase (albeit in an amount that is less than about 50 wt %, in some embodiments less than about 40 wt %, in some embodiments less than about 35 wt %, in some embodiments less than about 30 wt %, in some embodiments less than about 25 wt %, in some embodiments less than about 20 wt %, in some embodiments less than about 15 wt %, in some embodiments less than about 10 wt %, in some embodiments less than about 5 wt %, in some embodiments less than about 3 wt %, and in some embodiments less than about 1 wt %). The use of such a substantially water-insoluble ester of a phosphorous oxo acid in accordance with the present teachings stands in stark contrast to conventional wisdom which advocates removal of metathesis catalyst with a water-soluble phosphine, such as THMP (e.g., International Patent Application Publication No. WO 01/36368 A2).

Thus, as described above, after the isomerization suppression agent has been added to the mixture comprising the olefin metathesis product and residual metathesis catalyst, the isomerization suppression agent, in some embodiments, can be left in the mixture and carried along, either in whole or in part, in a subsequent chemical reaction or processing step. In other embodiments, including but not limited to embodiments in which the isomerization suppression agent comprises (i) an at least partially water-soluble salt and/or ester of a phosphorous oxo acid, and/or (ii) an at least partially water-soluble derivative of the phosphorous oxo acid in which at least one P—H bond has been replaced by a P—C bond, and/or (iii) an at least partially water-soluble salt and/or ester of the derivative, the isomerization suppression agent can optionally be separated and removed from the mixture, either partially or completely, prior to any subsequent reaction or processing step.

For embodiments in which it is desirable to separate and/or remove isomerization suppression agent following passivation of residual metathesis catalyst, a method in accordance with the present teachings can optionally further comprise washing or extracting the metathesis reaction mixture with a polar solvent (e.g., particularly, though not exclusively, for embodiments in which the isomerization suppression agent is at least partially soluble in the polar solvent). In some embodiments, the polar solvent is at least partially non-miscible with the mixture, such that a separation of layers can occur. In some embodiments, at least a portion of the isomerization suppression agent is partitioned into the polar solvent layer, which can then be separated from the non-miscible remaining layer and removed. Representative polar solvents for use in accordance with the present teachings include but are not limited to water, alcohols (e.g., methanol, ethanol, etc.), ethylene glycol, glycerol, DMF, multifunctional polar compounds including but not limited to polyethylene glycols and/or glymes, and the like, and combinations thereof. In some embodiments, the mixture is extracted with water. In some embodiments, when the ester of the phosphorous oxo acid used as an isomerization suppression agent is a phosphite ester that is at least partially hydrolyzable (e.g., in some embodiments, a phosphite ester having a low molecular weight, including but not limited to trimethyl phosphite, triethyl phosphite, and a combination thereof), washing the mixture with water may convert the phosphite ester into a corresponding acid. While neither desiring to be bound by any particular theory nor intending to limit in any measure the scope of the appended claims or their equivalents, it is presently believed that such a hydrolysis may occur more rapidly with lower molecular weight esters.

In addition to or as an alternative to washing the mixture with a polar solvent to remove isomerization suppression agent—which, in some embodiments, may serve to remove at least a portion of the isomerization suppression agent—a method in accordance with the present teachings can optionally further comprise removing at least a portion of the isomerization suppression agent by adsorbing it onto an adsorbent, which optionally can then be physically separated from the mixture (e.g., via filtration or the like). In some embodiments, the adsorbent is polar. Representative adsorbents for use in accordance with the present teachings include but are not limited to carbon, silica, silica-alumina, alumina, clay, magnesium silicates (e.g., Magnesols), the synthetic silica adsorbent sold under the tradename TRISYL by W. R. Grace & Co., diatomaceous earth, and the like, and combinations thereof.

In some embodiments, the olefin metathesis product comprises at least one terminal double bond and, in some embodiments, the isomerization comprises conversion of the terminal double bond to an internal double bond. In some embodiments, the olefin metathesis product comprises at least one internal double bond and, in some embodiments, the isomerization comprises conversion of the internal double bond to a different internal double bond (i.e., an internal double bond between two carbon atoms at least one of which was not part of the original internal double bond). In some embodiments, the olefin metathesis product comprises at least one internal double bond and, in some embodiments, the isomerization comprises conversion of the internal double bond to a terminal double bond. In some embodiments, the suppressing of the isomerization comprises an observed degree of isomerization that is less than about 5%, in some embodiments less than about 4%, in some embodiments less than about 3%, in some embodiments less than about 2%, in some embodiments less than about 1%, in some embodiments less than about 0.9%, in some embodiments less than about 0.8%, in some embodiments less than about 0.7%, in some embodiments less than about 0.6%, in some embodiments less than about 0.5%, in some embodiments less than about 0.4%, in some embodiments less than about 0.3%, in some embodiments less than about 0.2%, and in some embodiments less than about 0.1%.

In some embodiments, the olefin metathesis product is α,ω-di-functionalized. In some embodiments, the olefin metathesis product comprises a carboxylic acid moiety. In some embodiments, the olefin metathesis product comprises a terminal olefin and a carboxylic acid moiety. In some embodiments, the olefin metathesis product comprises an internal olefin and a carboxylic acid moiety. In some embodiments, the olefin metathesis product comprises a carboxylic ester moiety. In some embodiments, the olefin metathesis product comprises a terminal olefin and a carboxylic ester moiety. In some embodiments, the olefin metathesis product comprises an internal olefin and a carboxylic ester moiety. In some embodiments, the olefin metathesis product is selected from the group consisting of 9-decenoic acid, an ester of 9-decenoic acid, 9-undecenoic acid, an ester of 9-undecenoic acid, 9-dodecenoic acid, an ester of 9-dodecenoic acid, 1-decene, 2-dodecene, 3-dodecene, and combinations thereof. In some embodiments, the esters of 9-decenoic acid, 9-undecenoic acid, and 9-dodecenoic acid are alkyl esters, and, in some embodiments, methyl esters (e.g., methyl 9-decenoate, methyl 9-undecenoate, methyl 9-dodecenoate, etc.).

In some embodiments, the olefin metathesis product is derived from a natural oil reactant. In some embodiments, the metathesis reaction that produced the olefin metathesis product comprises self-metathesis of a natural oil and/or a derivative thereof. In some embodiments, the metathesis reaction that produced the olefin metathesis product comprises cross-metathesis between a natural oil and/or a derivative thereof and a low molecular weight olefin.

Representative examples of natural oils for use in accordance with the present teachings include but are not limited to vegetable oils, algal oils, animal fats, tall oils (e.g., by-products of wood pulp manufacture), derivatives of these oils, and the like, and combinations thereof. Representative examples of vegetable oils for use in accordance with the present teachings include but are not limited to canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, hemp oil, castor oil, and the like, and combinations thereof.

Representative examples of animal fats for use in accordance with the present teachings include but are not limited to lard, tallow, poultry fat, yellow grease, brown grease, fish oil, and the like, and combinations thereof. In some embodiments, the natural oil may be refined, bleached, and/or deodorized.

Representative examples of natural oil derivatives for use in accordance with the present teachings include but are not limited to gums, phospholipids, soapstock, acidulated soapstock, distillate or distillate sludge, fatty acids, fatty acid alkyl esters (e.g., non-limiting examples such as 2-ethylhexyl ester, etc.), hydroxy-substituted variations thereof, and the like, and combinations thereof. In some embodiments, the natural oil derivative is a fatty acid methyl ester (FAME) derived from the glyceride of the natural oil.

In some embodiments, the low-molecular-weight olefin is an "α-olefin" (aka "terminal olefin") in which the unsaturated carbon-carbon bond is present at one end of the compound. In some embodiments, the low-molecular-weight olefin is an internal olefin. In some embodiments, the low-molecular-weight olefin is functionalized. In some embodiments, the low-molecular weight olefin is a $C_2$-$C_{30}$ olefin. In some embodiments, the low-molecular weight olefin is a $C_2$-$C_{30}$ α-olefin. In some embodiments, the low-molecular weight olefin is a $C_2$-$C_{25}$ olefin. In some embodiments, the low-molecular weight olefin is a $C_2$-$C_{25}$ α-olefin. In some embodiments, the low-molecular weight olefin is a $C_2$-$C_{20}$ olefin. In some embodiments, the low-molecular weight olefin is a $C_2$-$C_{20}$ α-olefin. In some embodiments, the low-molecular weight olefin is a $C_2$-$C_{15}$ olefin. In some embodiments, the low-molecular weight olefin is a $C_2$-$C_{15}$ α-olefin. In some embodiments, the low-molecular weight olefin is a $C_2$-$C_{10}$ olefin. In some embodiments, the low-molecular weight olefin is a $C_2$-$C_{10}$ α-olefin. In some embodiments, the low-molecular weight olefin is a $C_2$-$C_8$ olefin. In some embodiments, the low-molecular weight olefin is a $C_2$-$C_8$ α-olefin. In some embodiments, the low-molecular weight olefin is a $C_2$-$C_6$ olefin. In some embodiments, the low-molecular weight olefin is a $C_2$-$C_6$ α-olefin. Representative low-molecular-weight olefins in the $C_2$ to $C_6$ range include but are not limited to ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, 1-hexene, 2-hexene, 3-hexene, cyclohexene, and the like, and combinations thereof. In some embodiments, the low-molecular-weight olefin is an α-olefin selected from the group consisting of styrene, vinyl cyclohexane, and a combination thereof. In some embodiments, the low-molecular weight olefin is a mixture of linear and/or branched olefins in the $C_4$-$C_{10}$ range. In some embodiments, the low-molecular weight olefin is a mixture of linear and/or branched $C_4$ olefins (e.g., combinations of 1-butene, 2-butene, and/or iso-butene). In some embodiments, the low-molecular weight olefin is a mixture of linear and/or branched olefins in the higher $C_{11}$-$C_{14}$ range.

In some embodiments, the olefin metathesis product comprises at least one internal double bond, which in some embodiments is cis and in some embodiments is trans. In some embodiments, the olefin metathesis product comprises at least one terminal double bond and at least one internal double bond. In some embodiments, the olefin metathesis product comprises at least one terminal double bond and/or at least one internal double bond, and at least one additional functional group. In some embodiments, the at least one additional functional group is selected from the group consisting of carboxylic acids, carboxylic esters, mono-acylglycerides (MAGs), di-acylglycerides (DAGs), tri-acylglycerides (TAGs), and combinations thereof. In some embodiments, the olefin metathesis product is produced in a self-metathesis reaction. In some embodiments, the olefin metathesis product is produced in a cross-metathesis reaction. In some embodiments, the olefin metathesis product is a downstream derivative of a self-metathesis or cross-metathesis product (including but not limited to, for example, transesterification products, hydrolysis products, and the like, and combinations thereof). In some embodiments, the olefin metathesis product is produced in a metathesis reaction involving one or more previously formed olefin metathesis products (e.g., the production of 9-ODDAME from the cross-metathesis of 9-DAME and 9-DDAME—one or both of which is itself a product of a metathesis reaction).

In some embodiments, the metathesis reaction that produced the olefin metathesis product comprises the reaction of two triglycerides present in a natural feedstock in the presence of a metathesis catalyst (self-metathesis), wherein each triglyceride comprises at least one carbon-carbon double bond, thereby forming a new mixture of olefins and esters that in some embodiments comprises a triglyceride dimer. In some embodiments, the triglyceride dimer comprises more than one carbon-carbon double bond, such that higher oligomers also can form. In some embodiments, the metathesis reaction that produced the olefin metathesis product comprises the reaction of an olefin (e.g., a low-molecular weight olefin) and a triglyceride in a natural feedstock that comprises at least one carbon-carbon double bond, thereby forming new olefinic molecules as well as new ester molecules (cross-metathesis).

In some embodiments, the residual metathesis catalyst comprises a transition metal. In some embodiments, the residual metathesis catalyst comprises ruthenium. In some embodiments, the residual metathesis catalyst comprises rhenium. In some embodiments, the residual metathesis catalyst comprises tantalum. In some embodiments, the residual metathesis catalyst comprises nickel. In some embodiments, the residual metathesis catalyst comprises tungsten. In some embodiments, the residual metathesis catalyst comprises molybdenum.

In some embodiments, the residual metathesis catalyst comprises a ruthenium carbene complex and/or an entity derived from such a complex. In some embodiments, the residual metathesis catalyst comprises a material selected from the group consisting of a ruthenium vinylidene complex, a ruthenium alkylidene complex, a ruthenium methylidene complex, a ruthenium benzylidene complex, and combinations thereof, and/or an entity derived from any such complex or combination of such complexes. In some embodiments, the residual metathesis catalyst comprises a ruthenium carbene complex comprising at least one tricyclohexylphosphine ligand and/or an entity derived from such a complex. In some embodiments, the residual metathesis catalyst comprises a ruthenium carbene complex comprising at least two tricyclohexylphosphine ligands [e.g., $(PCy_3)_2 Cl_2Ru=CH-CH=C(CH_3)_2$, etc.] and/or an entity derived from such a complex. In some embodiments, the residual metathesis catalyst comprises a ruthenium carbene complex comprising at least one imidazolidine ligand and/or an entity derived from such a complex. In some embodiments, the residual metathesis catalyst comprises a ruthenium carbene complex comprising an isopropyloxy group attached to a benzene ring and/or an entity derived from such a complex.

In some embodiments, the residual metathesis catalyst comprises a Grubbs-type olefin metathesis catalyst and/or an entity derived therefrom. In some embodiments, the residual metathesis catalyst comprises a first-generation Grubbs-type olefin metathesis catalyst and/or an entity derived therefrom. In some embodiments, the residual metathesis catalyst comprises a second-generation Grubbs-type olefin metathesis catalyst and/or an entity derived therefrom. In some embodiments, the residual metathesis catalyst comprises a first-generation Hoveda-Grubbs-type olefin metathesis catalyst and/or an entity derived therefrom. In some embodiments, the residual metathesis catalyst comprises a second-generation Hoveda-Grubbs-type olefin metathesis catalyst and/or an entity derived therefrom. In some embodiments, the residual metathesis catalyst comprises one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

Representative phosphorous oxo acids for use in accordance with the present teachings include but are not limited to those described in F. A. Cotton and G. Wilkinson's *Advanced Inorganic Chemistry, Fifth Edition*, New York: John Wiley & Sons, 1988, pages 382-443. By way of illustration, representative phosphorous oxo acids include but are not limited to phosphorous acid ($H_3PO_3$, aka "phosphonic acid"), phosphinic acid ($H_3PO_2$, aka "hypophosphorous acid), phosphoric acid ($H_3PO_4$, aka "orthophosphoric acid), pyrophosphoric acid ($H_4P_2O_7$), polyphosphoric acids, ultraphosphonic acid ($H_2P_4O_{11}$), di- and polyacids of phosphorous in lower formal oxidation states that comprise P—H and/or P—P bonds, and the like, and salts and anions thereof, and the like, and combinations thereof.

In some embodiments, the phosphorous oxo acid comprises a higher acid. In some embodiments, the higher acid comprises phosphoric acid. In some embodiments, the ester of the phosphoric acid is selected from the group consisting of mono-esters, di-esters, tri-esters, and combinations thereof. In some embodiments, the ester of the phosphoric acid comprises a mono-ester. In some embodiments, the mono-ester of phosphoric acid is not monophenyl phosphoester [P(O)(OPh)(OH)$_2$].

In some embodiments, the phosphorous oxo acid comprises a lower acid. In some embodiments, the lower acid is selected from the group consisting of phosphorous acid, phosphinic acid, and a combination thereof. In some embodiments, the phosphorous oxo acid comprises phosphorous acid. In some embodiments, as shown in FIG. 1, the ester of the phosphorous acid is selected from the group consisting of mono-esters, di-esters, tri-esters, and combinations thereof. In some embodiments, the ester of the phosphorous acid comprises a tri-ester. In some embodiments, the isomerization suppression agent comprises a phosphite ester. In some embodiments, the phosphite ester comprises a structure $P(OR^1R^2R^3)_3$, wherein $R^1$, $R^2$, and $R^3$ are alike or different and are each independently selected from the group consisting of substituted or unsubstituted $C_1$-$C_{100}$ alkyl, substituted or unsubstituted aryl, and combinations thereof, and wherein covalent bonds may optionally exist between two or more of $R^1$, $R^2$, and $R^3$, such that when two or more of $R^1$, $R^2$, and $R^3$ are taken together, a bidentate or tridentate ligand to phosphorous is formed.

In some embodiments, the phosphite ester is selected from the group consisting of aryl organophosphites, alkyl organophosphites, aryl-alkyl mixed organophosphites, and combinations thereof. In some embodiments, the phosphite ester comprises one or a plurality of the high molecular weight phosphites commercially available from Dover Chemical Corporation of Dover, Ohio and/or Galata Chemicals of Southbury, Conn. Representative phosphites from Dover Chemical Corporation for use in accordance with the present teachings include both liquids and solids, and include but are not limited to those sold under the following product names as well as combinations thereof: trisnonylphenyl phosphite (DOVERPHOS® 4), trisnonylphenyl phosphite (+0.75% triisopropanolamine) (DOVERPHOS® 4-HR), trisnonylphenyl phosphite (+1.0% triisopropanolamine) (DOVERPHOS® 4-HR Plus), trisnonylphenyl phosphite containing maximum residual nonylphenol of 0.1% (DOVERPHOS® HIPURE 4), trisnonylphenyl phosphite (+0.75% triisopropanolamine) containing maximum residual nonylphenol of 0.1% (DOVERPHOS® HIPURE 4-HR), diphenyl phosphite (DOVERPHOS® 213), triphenyl phosphite (DOVERPHOS® 10), phenyl diisodecyl phosphite (DOVERPHOS® 7), diphenyl isodecyl phosphite (DOVERPHOS® 8), diphenyl isooctyl phosphite (DOVERPHOS® 9), tetraphenyl dipropyleneglycol diphosphite (DOVERPHOS® 11), poly (dipropyleneglycol) phenyl phosphite (DOVERPHOS® 12), $C_{12}$-$C_{15}$ alkyl bisphenol A phosphite (DOVERPHOS® 613), $C_{10}$ alkyl bisphenol A phosphite (DOVERPHOS® 675), triisodecyl phosphite (DOVERPHOS® 6), tris(tridecyl) phosphite (DOVER- PHOS® 49), trilauryl phosphite (DOVERPHOS® 53), tris (dipropylene glycol) phosphite (DOVERPHOS® 72), dioleyl hydrogen phosphite (DOVERPHOS® 253), tris(2,4-di-tert-butylphenyl) phosphite (DOVERPHOS® S-480), distearyl pentaerythritol diphosphite (DOVERPHOS® S-680), distearyl pentaerythritol diphosphite (+triisopropanolamine) (DOVERPHOS® S-682), bis(2,4-dicumylphenyl) pentaerythritol diphosphite (DOVERPHOS® S-9228), and the like, and combinations thereof. Representative phosphites from Galata Chemicals for use in accordance with the present teachings include both liquids and solids, and include but are not limited to those sold under the following product names as well as combinations thereof: tris (nonylphenyl) phosphite, diphenyl phosphite, triphenyl phosphite, phenyl diisodecyl phosphite, diphenyl isodecyl phosphite, dodecyl nonylphenol phosphite blend, triisodecyl phosphite, triisotridecyl phosphite, 2-ethylhexyl diphenyl phosphite, poly (dipropylene glycol) phenyl phosphite, tetraphenyl dipropyleneglycol diphosphite, trilauryl phosphite, phenyl neopentylene glycol phosphite, heptakis (dipropyleneglycol) triphosphite, trilauryl trithio phosphite, diphenyl tridecyl phosphite, tris (dipropyleneglycol) phosphite, poly 4,4' isopropylidenediphenol-C10 alcohol phosphite, 4,4' isopropylidenediphenol-C12-15 alcohol phosphite, and the like, and combinations thereof.

In some embodiments, the derivative of the phosphorous acid in which at least one P—H bond has been replaced by a P—C bond comprises a phosphonic acid. In some embodiments, the ester of the derivative is selected from the group consisting of mono-esters, di-esters, and a combination thereof. In some embodiments, the ester comprises a phosphonate. In some embodiments, the ester comprises one or a plurality of the phosphonates commercially available from Thermphos International BV (Vlissingen, The Netherlands) and sold under the tradename DEQUEST. Representative phosphonates from Thermphos for use in accordance with the present teachings include but are not limited to those sold under the following product names as well as combinations thereof: amino trimethylene phosphonic acid and salts thereof (DEQUEST® 2000, DEQUEST® 2000EG, DEQUEST® 2000LC, DEQUEST® 2006), 1-hydroxyethylidene-1,1-diphosphonic acid and salts thereof (DEQUEST® 2010, DEQUEST® 2010CS, DEQUEST® 2010LA, DEQUEST® 2010LC, DEQUEST® 2014, DEQUEST® 2016, DEQUEST® 2016D, DEQUEST® 2016DG), DEQUEST® 2046, DEQUEST® 2047, DEQUEST® 2047G, diethylenetriamine penta(methylene phosphonic acid) and salts thereof (DEQUEST® 2060S, DEQUEST® 2066, DEQUEST® 2066A, DEQUEST® 2066C2), a proprietary polyamino phosphonic acid (DEQUEST® 2086), bis(hexamethylene triamine penta(methylene phosphonic acid)) and salts thereof (DEQUEST® 2090), diethylene triamine penta(methylene phosphonic acid) and salts thereof (DEQUEST® 4066), DEQUEST® 4266D, DEQUEST® 6004, and the like, and combinations thereof.

Figure 2:
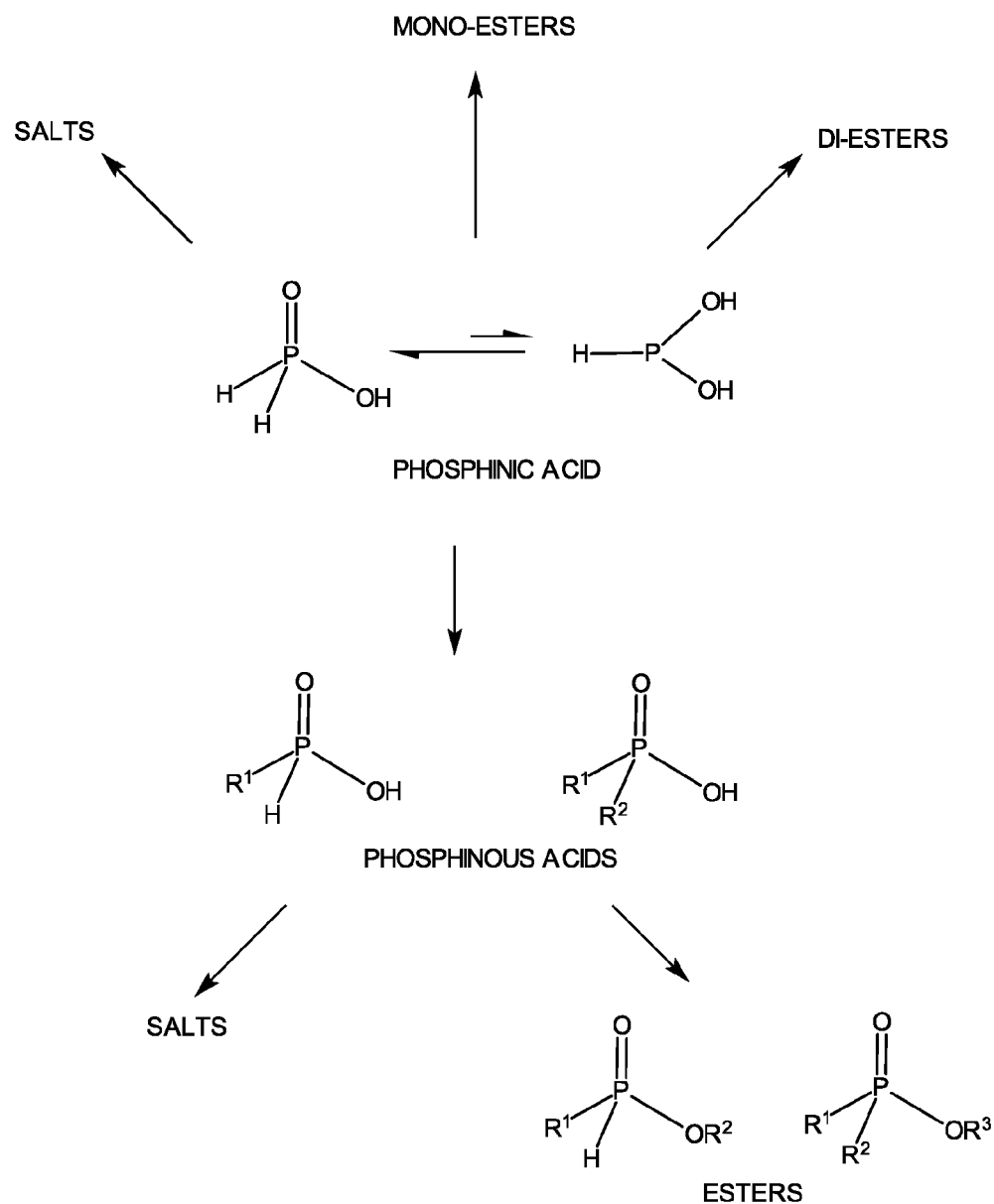
FIG. 2 shows representative phosphinic acid derivatives for use in accordance with the present teachings.

In some embodiments, as shown in FIG. 2, the phosphorous oxo acid comprises phosphinic acid. In some embodiments, the ester of the phosphinic acid is selected from the group consisting of mono-esters, di-esters, and a combination thereof. In some embodiments, the derivative of the phosphinic acid in which at least one P—H bond has been replaced by a P—C bond comprises a phosphinous acid. In some embodiments, the phosphinous acid is selected from the group consisting of $R^1HP(O)OH$, $R^2R^3P(O)OH$, and a combination thereof, wherein $R^1$, $R^2$, and $R^3$ are alike or different and are each independently selected from the group consisting of substituted or unsubstituted $C_1$-$C_{100}$ alkyl, substituted or unsubstituted aryl, and combinations thereof, wherein a covalent bond may exist between $R^2$ and $R^3$, such that when $R^2$ and $R^3$ are taken together, a bidentate ligand to phosphorous is formed. In some embodiments, the ester of the phosphinous acid comprises a structure selected from the group consisting of $R^1HP(O)OR^2$, $R^3R^4P(O)OR^5$, and a combination thereof, wherein $R^1$, $R^2$, $R^3$, $R^4$, and $R^5$ are alike or different and are each independently selected from the group consisting of substituted or unsubstituted $C_1$-$C_{100}$ alkyl, substituted or unsubstituted aryl, and combinations thereof, wherein a covalent bond may exist between $R^1$ and $R^2$, such that when $R^1$ and $R^2$ are taken together, a bidentate ligand to phosphorous is formed, and wherein covalent bonds may optionally exist between two or more of $R^3$, $R^4$, and $R^5$, such that when two or more of $R^3$, $R^4$, and $R^5$ are taken together, a bidentate or tridentate ligand to phosphorous is formed.

In some embodiments, the isomerization suppression agent is attached to a solid support (e.g., silica gel) and comprises (i) a salt and/or an ester of a phosphorous oxo acid, and/or (ii) a derivative of the phosphorous oxo acid in which at least one P—H bond has been replaced by a P—C bond, and/or (iii) a salt and/or an ester of the derivative. In some embodiments, the solid support comprises one or more polar functional groups. Representative solid supports for use in accordance with the present teachings include but are not limited to carbon, silica, silica-alumina, alumina, clay, magnesium silicates (e.g., Magnesols), the synthetic silica adsorbent sold under the tradename TRISYL by W. R. Grace & Co., diatomaceous earth, and the like, and combinations thereof.

In some embodiments, the isomerization suppression agent is added to a mixture in accordance with the present teachings in a molar excess relative to the residual metathesis catalyst. In some embodiments, the molar excess is at least about 2 to 1. In some embodiments, the molar excess is at least about 3 to 1. In some embodiments, the molar excess is at least about 4 to 1. In some embodiments, the molar excess is at least about 5 to 1. In some embodiments, the molar excess is at least about 10 to 1. In some embodiments, the molar excess is at least about 15 to 1. In some embodiments, the molar excess is at least about 20 to 1. In some embodiments, the molar excess is at least about 25 to 1. In some embodiments, the molar excess is at least about 30 to 1. In some embodiments, the molar excess is at least about 35 to 1. In some embodiments, the molar excess is at least about 40 to 1. In some embodiments, the molar excess is at least about 45 to 1. In some embodiments, the molar excess is at least about 50 to 1. In some embodiments, the molar excess is at least about 55 to 1. In some embodiments, the molar excess is at least about 60 to 1. In some embodiments, the molar excess is at least about 65 to 1. In some embodiments, the molar excess is at least about 70 to 1. In some embodiments, the molar excess is at least about 75 to 1. In some embodiments, the molar excess is at least about 80 to 1. In some embodiments, the molar excess is at least about 85 to 1. In some embodiments, the molar excess is at least about 90 to 1. In some embodiments, the molar excess is at least about 95 to 1. In some embodiments, the molar excess is at least about 100 to 1.

While neither desiring to be bound by any particular theory nor intending to limit in any measure the scope of the appended claims or their equivalents, it is presently believed that as the organic solubility of an isomerization suppression agent in accordance with the present teachings increases, the molar excess of isomerization suppression agent to residual metathesis catalyst may decrease without substantially diminishing the efficacy of isomerization suppression. Moreover, while neither desiring to be bound by any particular theory nor intending to limit in any measure the scope of the appended claims or their equivalents, it is presently believed that when high shear mixing is employed, the molar excess of isomerization suppression agent to residual metathesis catalyst may decrease without substantially diminishing the efficacy of isomerization suppression.

In some embodiments, the conditions under which an isomerization suppression agent in accordance with the present teachings is added to a mixture that comprises an olefin metathesis product and residual metathesis catalyst comprise mixing. In some embodiments, the mixing comprises high shear mixing (e.g., mixing of a type sufficient to disperse and/or transport at least a portion of a first phase and/or chemical species into a second phase with which the first phase and/or a chemical species would normally be at least partly immiscible).

In some embodiments, the conditions under which an isomerization suppression agent in accordance with the present teachings is added to a mixture that comprises an olefin metathesis product and residual metathesis catalyst comprise heating. The present teachings are in no way restricted to any particular heating temperature or range of temperatures. However, for purposes of illustration, in some embodiments, the conditions under which an isomerization suppression agent in accordance with the present teachings is added to a mixture that comprises an olefin metathesis product and residual metathesis catalyst comprise a heating temperature of about 40° C. or higher. In some embodiments, the heating comprises a temperature of about 50° C. or higher. In some embodiments, the heating comprises a temperature of about 60° C. or higher. In some embodiments, the heating comprises a temperature of about 70° C. or higher. In some embodiments, the heating comprises a temperature of about 80° C. or higher. In some embodiments, the heating comprises a temperature of about 90° C. or higher.

The present teachings are in no way restricted to any particular duration of residence time. However, for purposes of illustration, in some embodiments, the conditions under which an isomerization suppression agent in accordance with the present teachings is added to a mixture that comprises an olefin metathesis product and residual metathesis catalyst comprise a residence time of at least about 1 minute. In some embodiments, the conditions comprise a residence time of at least about 2 minutes. In some embodiments, the conditions comprise a residence time of at least about 3 minutes. In some embodiments, the conditions comprise a residence time of at least about 4 minutes. In some embodiments, the conditions comprise a residence time of at least about 5 minutes. In some embodiments, the conditions comprise a residence time of at least about 10 minutes. In some embodiments, the conditions comprise a residence time of at least about 15 minutes. In some embodiments, the conditions comprise a residence time of at least about 20 minutes. In some embodiments, the conditions comprise a residence time of at least about 25 minutes. In some embodiments, the conditions comprise a residence time of at least about 30 minutes. In some embodiments, the conditions comprise a residence time of at least about 35 minutes. In some embodiments, the conditions comprise a residence time of at least about 40 minutes. In some embodiments, the conditions comprise a residence time of at least about 45 minutes. In some embodiments, the conditions comprise a residence time of at least about 50 minutes. In some embodiments, the conditions comprise a residence time of at least about 55 minutes. In some embodiments, the conditions comprise a residence time of at least about 60 minutes. In some embodiments, the conditions comprise a residence time of one or more hours.

In some embodiments, the conditions under which an isomerization suppression agent in accordance with the present teachings is added to a mixture that comprises an olefin metathesis product and residual metathesis catalyst comprise mixing, heating, and/or a residence time of at least about 2 minutes.

As presently contemplated, the addition of an isomerization suppression agent to a mixture that comprises an olefin metathesis product and residual metathesis catalyst in accordance with the present teachings can be practiced whenever it is desirable to prevent isomerization of an olefin metathesis product—particularly though not exclusively potentially labile olefin products, such as terminal olefins—during any subsequent handling and/or processing including but not limited to heating, distillation, photolytic exposure, exposure to oxidants, and the like, and combinations thereof.

In some embodiments, methods for suppressing isomerization of an olefin metathesis product in accordance with the present teachings can be used in combination with metathesis-based methods for refining natural oil feedstocks. Representative metathesis-based methods for refining natural oil feedstocks include but are not limited to those described in United States Patent Application Publication No. 2011/0113679 A1, assigned to the assignee of the present invention.

By way of non-limiting example, in reference to FIG. 1 of United States Patent Application Publication No. 2011/0113679 A1, methods for suppressing isomerization of an olefin metathesis product in accordance with the present teachings can be implemented prior to introducing the metathesized product 22 to the separation unit 30 (e.g., a distillation column) and/or at one or more additional stages in the process. By way of further non-limiting example, in reference to FIG. 2 of United States Patent Application Publication No. 2011/0113679 A1, methods for suppressing isomerization of an olefin metathesis product in accordance with the present teachings can be implemented prior to introducing the metathesized product 122 to the separation unit 130 and/or the hydrogenation unit 125 and/or at one or more additional stages in the process. Moreover, in some embodiments, when the isomerization suppression agent has sufficient thermal stability (e.g., a phosphite ester having a sufficiently high molecular weight), the isomerization suppression agent can be left in the mixture comprising the olefin metathesis product and carried along for further processing (e.g., to the separation units 30 and/or 130 shown, respectively, in FIGS. 1 and 2 of United States Patent Application Publication No. 2011/0113679 A1 and/or to one or more additional units in these or analogous systems).

Figure 3:
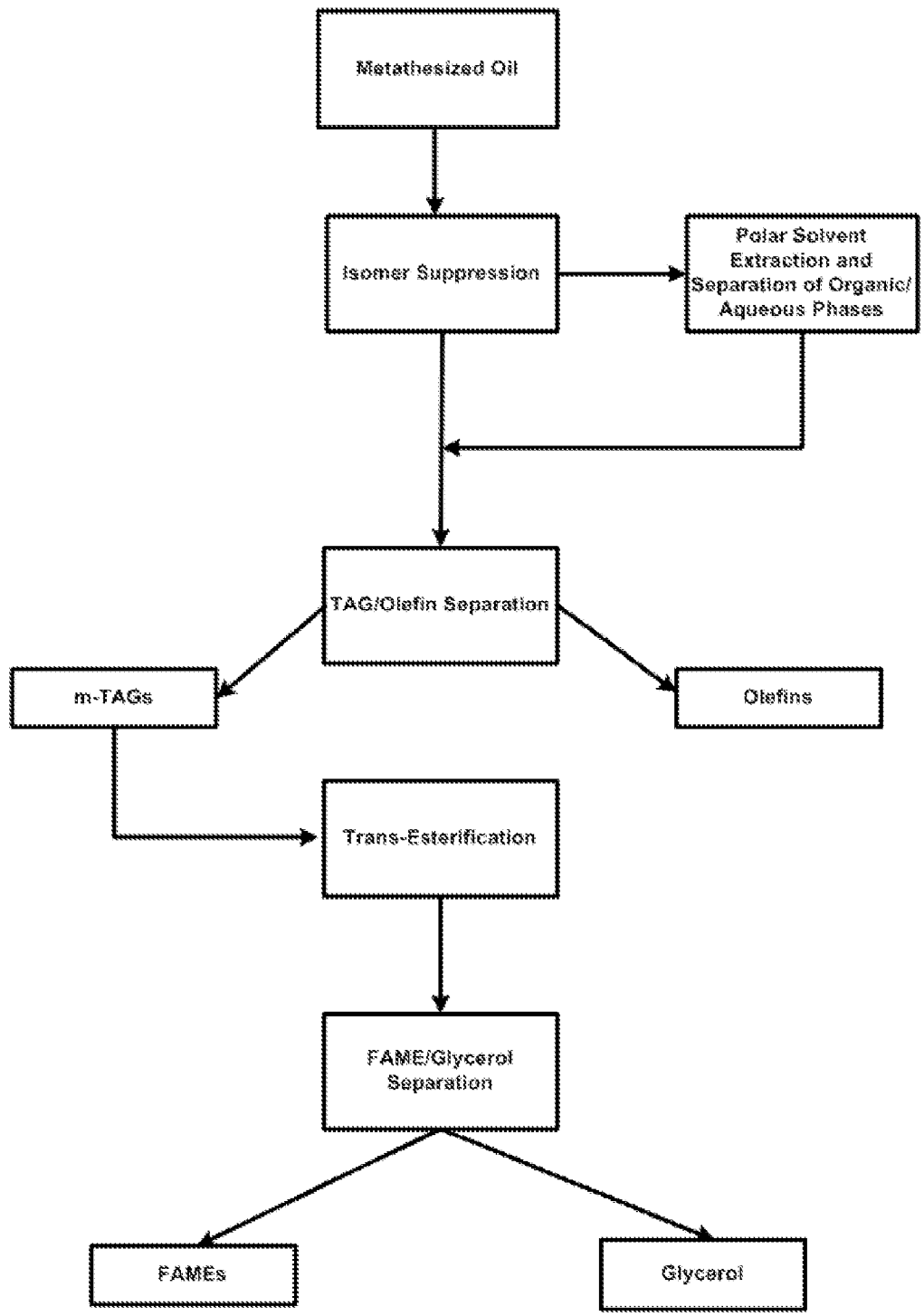
FIG. 3 is a process flow diagram depicting a representative scheme for isomerization suppression in an olefin metathesis product and shows an optional extraction, separation, and transesterification.

In some embodiments, as shown in FIG. 3, methods for suppressing isomerization of an olefin metathesis product in accordance with the present teachings may optionally further comprise a polar solvent wash—in other words, extracting the mixture to which an isomerization suppression agent has been added with a polar solvent. However, as described above, in some embodiments it may not be possible, necessary, and/or desirable to remove an isomerization suppression agent in accordance with the present teachings via extraction with a polar solvent prior to further processing, which in some embodiments includes but is not limited to processing involving heating.

In some embodiments, the metathesis mixture (e.g., a neat mixture that comprises, in some embodiments, natural oil, residual metathesis catalyst, olefin metathesis product and, optionally, low-molecular-weight olefin) is substantially immiscible with the polar solvent, such that two layers are formed. For the sake of convenience, these immiscible layers are described herein as being "aqueous" and "organic" although, in some embodiments, the so-called aqueous layer may be comprised of a polar solvent other than or in addition to water. In some embodiments, the polar solvent extraction (e.g., washing with water) can serve to remove at least a portion of the isomerization suppression agent—particularly though not exclusively when the isomerization suppression agent is at least partially hydrolyzable (e.g., in some embodiments, a phosphite ester having a low molecular weight, including but not limited to trimethyl phosphite, triethyl phosphite, and a combination thereof)—which, in some embodiments, can result in the conversion of an isomerization suppression agent in accordance with the present teachings (e.g., an ester of a phosphorous oxo acid) into a corresponding acid.

In some embodiments, when extraction with a polar solvent is desired, the extracting comprises high shear mixing although such mixing, in some embodiments, may contribute to undesirable emulsion formation. In some embodiments, the extracting comprises low-intensity mixing (e.g., stirring that is not high shear). The present teachings are in no way restricted to any particular type or duration of mixing. However, for purposes of illustration, in some embodiments, the extracting comprises mixing the polar solvent and the mixture together for at least about 1 minute. In some embodiments, the mixture and the polar solvent are mixed together for at least about 2 minutes, in some embodiments for at least about 5 minutes, in some embodiments for at least about 10 minutes, in some embodiments for at least about 15 minutes, in some embodiments for at least about 20 minutes, in some embodiments for at least about 25 minutes, in some embodiments for at least about 30 minutes, in some embodiments for at least about 35 minutes, in some embodiments for at least about 40 minutes, in some embodiments for at least about 45 minutes, in some embodiments for at least about 50 minutes, in some embodiments for at least about 55 minutes, and in some embodiments for at least about 60 minutes.

When extraction with a polar solvent is desired, the present teachings are in no way restricted to any particular amount of polar solvent added to the mixture for the extracting. However, for purposes of illustration, in some embodiments, the amount by weight of polar solvent (e.g., water) added to the mixture for the extracting is more than the weight of the mixture. In some embodiments, the amount by weight of polar solvent (e.g., water) added to the mixture for the extracting is less than the weight of the mixture. In some embodiments, the weight ratio of the mixture to the water added to the mixture is at least about 1:1, in some embodiments at least about 2:1, in some embodiments at least about 3:1, in some embodiments at least about 4:1, in some embodiments at least about 5:1, in some embodiments at least about 6:1, in some embodiments at least about 7:1, in some embodiments at least about 8:1, in some embodiments at least about 9:1, and in some embodiments at least about 10:1.

In some embodiments, when extraction with a polar solvent is desired, methods for suppressing isomerization of an olefin metathesis product in accordance with the present teachings further comprise allowing a settling period following the polar solvent wash to promote phase separation. The present teachings are in no way restricted to any particular duration of settling period. However, for purposes of illustration, in some embodiments, the settling period is at least about 1 minute. In some embodiments, the settling period is at least about 2 minutes. In some embodiments, the settling period is at least about 5 minutes. In some embodiments, the settling period is at least about 10 minutes. In some embodiments, the settling period is at least about 15 minutes.

In some embodiments, when extraction with a polar solvent is desired, methods for suppressing isomerization of an olefin metathesis product in accordance with the present teachings optionally further comprise separating an organic phase from an aqueous phase, as shown in FIG. 3. In some embodiments, particularly though not exclusively when the isomerization suppression agent is at least partially hydrolysable, a majority of the isomerization suppression agent is distributed in the aqueous phase. In some embodiments, a majority of the olefin metathesis product is distributed in the organic phase. In some embodiments, a majority of the isomerization suppression agent is distributed in the aqueous phase and a majority of the olefin metathesis product is distributed in the organic phase.

In some embodiments, when extraction with a polar solvent is desired, such that an organic phase is separated from an aqueous phase, and when the residual metathesis catalyst in the mixture comprises ruthenium, a majority of the ruthenium is carried into an organic phase and a minority of the ruthenium is distributed in an aqueous phase. In some embodiments, at least about 51% of the ruthenium is extracted into an organic phase. In some embodiments, at least about 60% of the ruthenium is extracted into an organic phase. In some embodiments, at least about 65% of the ruthenium is extracted into an organic phase. In some embodiments, at least about 70% of the ruthenium is extracted into an organic phase. In some embodiments, at least about 75% of the ruthenium is extracted into an organic phase. In some embodiments, at least about 80% of the ruthenium is extracted into an organic phase. In some embodiments, at least about 85% of the ruthenium is extracted into an organic phase. In some embodiments, at least about 90% of the ruthenium is extracted into an organic phase.

In some embodiments, it is observed that removing excess isomerization suppression agent from a cross-metathesized oil by washing with water can be accompanied by a loss in the overall efficacy of isomerization suppression. While neither desiring to be bound by any particular theory nor intending to limit in any measure the scope of the appended claims or their equivalents, it is presently believed that the reduction in isomerization suppression sometimes observed after a water wash is merely an artifact of handling. Moreover, it is presently believed that the effect can be mitigated and/or eliminated by using slightly different experimental conditions including but not limited to using higher concentrations of isomerization suppression agent, handling the material obtained from the suppression treatment under an inert atmosphere (e.g., nitrogen), and/or the like.

In some embodiments, as shown in FIG. 3, a method in accordance with the present teachings for suppressing isomerization of an olefin metathesis product produced in a metathesis reaction comprises: (a) adding an isomerization suppression agent to a mixture that comprises the olefin metathesis product and residual metathesis catalyst from the metathesis reaction under conditions that are sufficient to passivate at least a portion of the residual metathesis catalyst; and (b) processing the mixture to provide a fraction that comprises the olefin metathesis product and/or a derivative thereof, wherein the isomerization suppression agent is not removed from the mixture prior to the processing. The isomerization suppression agent comprises (i) a salt and/or an ester of a phosphorous oxo acid, and/or (ii) a derivative of the phosphorous oxo acid in which at least one P—H bond has been replaced by a P—C bond, and/or (iii) a salt and/or an ester of the derivative. In some embodiments, the ester of a phosphorous oxo acid is substantially water-insoluble. In some embodiments, the residual metathesis catalyst comprises ruthenium. In some embodiments, the fraction that comprises the olefin metathesis product and/or a derivative thereof is comprised primarily thereof (e.g., the olefin metathesis product and/or the derivative thereof account for at least about 51 wt % of the fraction, in some embodiments at least about 65 wt %, in some embodiments at least about 70 wt %, in some embodiments at least about 75 wt %, in some embodiments at least about 80 wt %, in some embodiments at least about 85 wt %, in some embodiments at least about 90 wt %, and in some embodiments at least about 95 wt %.

In some embodiments, the processing of the mixture comprises heating. In some embodiments, the processing of the mixture comprises heating to a temperature of at least about 100° C., in some embodiments at least about 125° C., in some embodiments at least about 150° C., in some embodiments at least about 175° C., in some embodiments at least about 200° C., in some embodiments at least about 225° C., and in some embodiments at least about 250° C. In some embodiments, the processing comprises distillation. In some embodiments, the processing comprises transesterification. In some embodiments, the processing comprises distillation and transesterification.

In some embodiments—particularly though not exclusively those involving metathesis-based methods for refining natural oil feedstocks—methods for suppressing isomerization of an olefin metathesis product in accordance with the present teachings further comprise separating the olefin metathesis product into a metathesized triacylglyceride (m-TAG) fraction and an olefinic fraction, as shown in FIG. 3. A majority of the triacylglyceride fraction is comprised by molecules comprising one or more carbon-carbon double bonds and, optionally, one or more additional functional groups, whereas a majority of the olefinic fraction is comprised by molecules comprising one or more unsaturated carbon-carbon bonds and no additional functional groups.

In some embodiments—particularly though not exclusively those involving metathesis-based methods for refining natural oil feedstocks—methods for suppressing isomerization of an olefin metathesis product in accordance with the present teachings further comprise transesterifying the triacylglyceride fraction to produce one or a plurality of transesterification products, as shown in FIG. 3. In some embodiments, the transesterification products comprise fatty acid methyl esters (FAMEs). In some embodiments—particularly though not exclusively those involving metathesis-based methods for refining natural oil feedstocks—methods for suppressing isomerization of an olefin metathesis product in accordance with the present teachings further comprise separating the transesterification products from a glycerol-containing phase, as shown in FIG. 3.

In some embodiments—particularly though not exclusively those involving metathesis-based methods for refining natural oil feedstocks—methods for suppressing isomerization of an olefin metathesis product in accordance with the present teachings further comprise separating the olefin metathesis product into a triacylglyceride fraction and an olefinic fraction, transesterifying the triacylglyceride fraction to produce one or a plurality of transesterification products (e.g., FAMEs), and separating the transesterification products from a glycerol-containing phase, as shown in FIG. 3. In some embodiments, the residual metathesis catalyst in the mixture comprises ruthenium. In some embodiments, a majority of the ruthenium is distributed between the glycerol-containing phase and the transesterification products.

In some embodiments, a method of refining a natural oil in accordance with the present teachings comprises (a) providing a feedstock comprising a natural oil; (b) reacting the feedstock in the presence of a metathesis catalyst to form a metathesized product comprising an olefin and an ester; (c) passivating the metathesis catalyst with an agent selected from the group consisting of (i) a salt and/or an ester of a phosphorous oxo acid, (ii) a derivative of the phosphorous oxo acid in which at least one P—H bond has been replaced by a P—C bond, (iii) a salt and/or an ester of the derivative, and (iv) combinations thereof; (d) separating the olefin in the metathesized product from the ester in the metathesized product; and (e) transesterifying the ester in the presence of an alcohol to form a transesterified product and/or hydrogenating the olefin to form a fully or partially saturated hydrogenated product.

As noted above, the use of THMP as an isomerization suppressor—particularly on an industrial scale—is problematic in view of its commercial availability and pricing, the fact that a carcinogenic byproduct, formaldehyde, typically accompanies its preparation, and the potential that exists to generate explosive $H_2$ gas if conditions become too basic. In addition to these drawbacks, the present inventors have found that when THMP (as opposed to an isomerization suppression agent in accordance with the present teachings) is used for the suppression of olefin isomerization—particularly when the amount of residual metathesis catalyst is low (e.g., in some embodiments less than about 1000 ppm, in some embodiments less than about 500 ppm, in some embodiments less than about 250 ppm, and in some embodiments less than about 100 ppm)—reclamation of transition metal from the residual metathesis catalyst can be complicated by the distribution of the transition metal (e.g., ruthenium) between multiple phases with no appreciable concentration or convergence of the transition metal into any one phase. By way of example, when THMP is used as an isomerization suppression agent in a metathesis-based method for refining a natural oil feedstock, such as described above, it is found that ruthenium is broadly distributed between a water wash stream on the one hand and a glycerol-containing phase and transesterification products on the other. In some studies, about 50% of the total ruthenium was carried into a water wash stream with the remaining Ru being distributed between a glycerol-containing phase and the transesterification products. While neither desiring to be bound by any particular theory nor intending to limit in any measure the scope of the appended claims or their equivalents, it is presently observed that the difficulty in concentrating a majority of the transition metal into a particular stream when THMP is used as the isomerization suppression agent arises primarily when the amount of ruthenium to be recovered is small (e.g., about 1 wt % or less). By contrast, when a large amount of ruthenium is involved (e.g., about 1 wt % or more) and THMP is used as the isomerization suppression agent, a majority of the ruthenium can be successfully concentrated into an aqueous phase and removed.

In some embodiments, for purposes of simplifying the metal reclamation process, it would be desirable if the metal to be reclaimed (e.g., in some embodiments, ruthenium) were concentrated primarily in one phase and, in some embodiments, if that phase were located downstream in the overall process. Thus, for embodiments in which the isomerization suppression agent has sufficient thermal stability (e.g., a phosphite ester having a sufficiently high molecular weight), such that it can be left in the mixture comprising the olefin metathesis product and carried along for further processing at high temperatures (e.g., 250° C.), a method in accordance with the present teachings provides a further advantage with respect to the use of THMP inasmuch as no aqueous wash is required up front in the process, and the catalyst metal can be more easily concentrated in and recovered from various bottom fractions downstream in the process.

Moreover, thermally stable isomerization suppression agents in accordance with the present teachings have reduced tendency to decompose into lower molecular weight phosphorus-containing compounds (e.g., phosphine, etc.) which could potentially contaminate the metathesis products. In addition, whereas it is oftentimes desirable to wash a suppressant such as THMP out of a metathesis mixture prior to subjecting the mixture to distillation and/or other high-temperature processing in order to avoid introducing the suppressant into hot areas of the process wherein decomposition and/or resultant product and/or recycle stream contamination can occur, the more thermally and hydrolytically stable isomerization suppression agents described herein can be carried through without water washing, which greatly simplifies metathesis-based methods for refining natural oil feedstocks by eliminating the need for (i) a water wash (mixing), (ii) separation (decanter), and (iii) recovery (evaporator).

The following examples and representative procedures illustrate features in accordance with the present teachings, and are provided solely by way of illustration. They are not intended to limit the scope of the appended claims or their equivalents.

EXAMPLES

Materials and Methods

Unless otherwise indicated, all chemicals were used as received and without drying. Palm oil was obtained from Wilmar International Limited. Kirkland soybean oil was purchased from retail sources. 1-Octene was purchased from Sigma Aldrich. C827 ruthenium catalyst was obtained from Materia, Inc. Trilauryl phosphite (DOVERPHOS® 53), trisnonyl phenyl phosphite (DOVERPHOS® 4), dioleyl hydrogen phosphite (DOVERPHOS® 253), and triisodecyl phosphite (DOVERPHOS® 6) were supplied by Dover Chemical Corporation. TNPP (along with other phosphites) was also supplied by Galata Chemicals. Diethyl phosphite was purchased from Aldrich (98% pure). Trimethyl phosphite was purchased from Aldrich (99+% pure). DEQUEST 0539 and DEQUEST 0520 were obtained from Thermphos International BV.

Unless otherwise specified, all isomerization results were derived from a small scale isomerization (SSI) unit as described below. By way of illustration, taking the amount of terminal-to-internal migration as a representative and non-limiting example, the degree of isomerization can be calculated by first obtaining the quotient of (i) the amount of internal isomers as represented, for example, by the areas under gas chromatograpy (GC) peaks corresponding to these internal isomers to (ii) the total amount of all isomers—both terminal and internal—as represented, for example, by the areas under the GC peaks corresponding to these isomers, and then multiplying this quotient by 100. Analogous calculations can be performed to determine the amount of internal-to-terminal migration and/or the amount of internal-to-internal migrations.

Example 1

Small Scale Isomerization (SSI) Studies

Metathesized samples were heated to 250° C. for one hour under nitrogen after suppression treatment. Duplicates runs were conducted on both the sample to be tested as well as a control sample which had not been treated. Degree of isomerization was determined by taking the total of isomers of methyl 9-decenoate divided by the total amount of methyl decenoate multiplied by 100.

The small scale isomerization unit includes a cylindrical aluminum block having several holes (e.g., six to eight) drilled therein. The aluminum block is placed on a hot plate and heated to the requisite temperature. Small amounts (typically several grams) of metathesis product are placed in glass tubes, which are then fitted with plastic heads providing an opening for a slight positive pressure of nitrogen to be present above the mixture. After purging the samples for 30 minutes under nitrogen, the mixtures are heated to 250° C. (with or without stirring) for one hour by placing the glass tubes in the opening of the aluminum block. The resulting triacylglycerides (TAGs) are then transesterified with methanol and base and the resulting FAMEs are analyzed by GC. In some embodiments, methyl 9-decenoate is measured vis-à-vis the amount of its internal isomers (if any).

Example 2

Preparation of a Cross-Metathesized Olefin Product

Octenylized palm oil was prepared as follows. At a 3:1 molar ratio, 1-octene (33.33 g) was added to palm oil (50 g) having a peroxide value below 2.0 (which can be obtained, typically, by heating the oil to approximately 200° C. under a $N_2$ sparge to thermally decompose peroxides). As used herein, the mole ratio of cross agent (e.g., 1-octene) to oil relates to the molar ratio of double bond content. In the oil, the double bond content is calculated from the relative ratio of the key fatty acids present (each with its own olefin content), all of which can be readily determined by gas chromatography after transesterification. Thus, in this example, a 3:1 mole ratio refers to having a 3:1 ratio of cross agent double bonds to the total double bonds of the oil. The resultant material was heated with stirring to 60° C. with nitrogen sparging for 30-45 minutes. Once oxygen has been removed, the nitrogen line was pulled up out of the oil into the headspace. The C827 catalyst (2.75 mg, approximately 55 ppm loading) was then added. The reaction was run for two hours with periodic sampling of the oil to determine the extent of conversion of the reaction.

Example 3

Phosphite Ester as Isomerization Suppression Agent

To 25 grams of cross-metathesized palm oil (3:1 octenylized at a loading of 55 ppm C827) was added an approximately 20-fold molar excess of DOVERPHOS® 53 (molar in relation to the amount of C827 present). This 20-fold molar excess relates to the amount of suppression agent added compared directly to the amount (moles) of catalyst present. The addition did not result in any observable separation, which suggested that the added phosphite was soluble in the oil. The mixture was then heated to 90° C. for one hour with stirring. The level of isomerization in the absence of any suppression agent was measured at 5.0% and 5.8% (duplicate runs) using a small scale isomerization (SSI) unit run at 250° C. for one hour. A portion of the suppressed sample was treated with water (approx 4:1 oil:water) and then separated. Both the water-washed and unwashed samples were tested for suppression.

Samples that were taken after the one-hour suppression reaction exhibited levels of isomerization of 0.1% and 0.2% (duplicate runs) after being run in the SSI unit. The water-washed samples exhibited similarly low levels of suppression (0.3% and 0.2%).

Example 4

Phosphite Ester as Isomerization Suppression Agent

A larger-scale reaction analogous to that described in Example 3 above was run using DOVERPHOS® 53 at a 20-fold molar excess over catalyst. A cross-metathesized palm oil (175 grams, 3:1 octenylized at a loading of 55 ppm C827) was added to a 500-mL three-necked, round-bottomed flask fitted with a nitrogen inlet/outlet and a distillation head. The sample was heated and stirred to 90° C. under nitrogen. At temperature, DOVERPHOS® 53 (107.5 microliters) was added to the mixture. The mixture was then heated for one hour at temperature. The heating was then increased to a point where the internal oil temperature was 250° C. A sample was taken at this "zero time" and the flask was then heated under these conditions (with the light olefins distilling) for two hours. Additional samples were taken at 80 and 120 minutes. The samples were all transesterified and then run for isomerization level by GC. The analysis showed that all of the samples (0, 80, and 120 minutes) had isomerization levels less that 0.4 wt %. Typical levels of isomerization of the non-suppressed material under similar conditions were 30+%.

Example 5

Phosphite Ester as Isomerization Suppression Agent

It was found that lowering the overall amount of phosphite (e.g., from a 20-fold molar excess to a 10-fold molar excess) still resulted in good isomerization suppression but at levels somewhat higher than reported in the above examples (e.g., typically up to 1%). A cross-metathesized palm oil (25 grams, 3:1 octenylized) was heated to 90° C. under nitrogen. At approximately 80° C., a 1:1 mixture by weight of DOVERPHOS® 4 in toluene (20 microliters) was added. The toluene was added to cut the overall viscosity of the phosphite being used. After 15 minutes, a sample was taken for SSI testing. A second sample was taken after one hour. Both samples showed significant suppression of isomerization. The results are summarized in Table 1 below.

This example demonstrates the concept that prior dissolution of the isomerization suppression agent can be performed (e.g., by dissolving a phosphite ester in a solvent) and, in some embodiments, may be desirable (e.g., to cut the overall viscosity, better solubilize the phosphite ester, etc).

In this experiment, it was also noted that a reduction in reaction time from 60 minutes of treatment at 90° C. to only 15 minutes gave similar isomerization suppression results. Thus, while neither desiring to be bound by any particular theory nor intending to limit in any measure the scope of the appended claims or their equivalents, it is presently believed that increased solubility in organic systems of an isomerization suppression agent in accordance with the present teachings can result in shorter residence times and/or lower reaction temperatures without substantially affecting the efficacy of isomerization suppression.

Example 6

Low Molecular Weight Phosphite Ester as Isomerization Suppression Agent

A cross-metathesized palm oil (15.1 grams, 1:1 octenylized) was sparged with $N_2$ for 45 minutes. At this time, trimethyl phosphite (60 microliters) was added to the reaction mixture. The mixture was heated with stirring for one hour at 90° C. The isomerization level of this material after reaction in the SSI unit (one hour at 250° C.) was 0.4%. The non-suppressed control was found to undergo 25.9% isomerization when run in SSI, as shown in Table 1 below.

Example 7

Phosphonate as Isomerization Suppression Agent

To 20 grams of a cross-metathesized palm oil (3:1 octenylized) was added DEQUEST® 539 (80 microliters, further diluted from the active ingredient to approximately 1 M), which represented an approximately 100-fold ratio of the phosphonate to the catalyst. The mixture was heated for one hour under nitrogen at 90° C. A sample was then taken for SSI testing. The material was then water washed and another sample was taken of the washed material for SSI. The sample having no water washing showed an isomerization level of 2.0%/2.5% (duplicate runs) versus the unsuppressed sample (40.3% isomerization), as shown by the data in Table 1 below. The water-washed sample gave isomerization levels of 7.6%/7.8% (duplicate runs), which is still lower than the control but not as efficacious as leaving the phosphonates in the metathesized material.

Example 8

Susceptibility of Isomerization Suppression Agent to Distillation

To determine whether an isomerization suppression agent in accordance with the present teachings would distill under typical natural oil refining conditions (e.g., 250° C., 15 mm), DOVERPHOS® 6 (30 g) was charged to a 100-mL, three-necked, round-bottomed flask fitted with a J-KEM® temperature controller probe and a simple distillation head. The pot temperature was set to 275° C. at a reduced pressure of 10 mm Hg. No change in overhead temperature was detected at a pot temperature of 255° C. At a pot temperature of 264° C., the overhead temperature rose over time to 210° C. but no liquid distillate was observed. Reducing the vacuum to 5 mm Hg resulted in a small amount of liquid overhead (215° C. overhead). At 2 mm Hg, a small amount of overhead was collected (242° C. bottoms and 222° C. overhead). A total of 1.5 grams was collected (5% of charge).

Running the same experiment with DOVERPHOS® 4 resulted in no overhead product at a bottoms temperature of 280° C. and a reduced pressure of 2 mm Hg (160° C. overhead). While neither desiring to be bound by any particular theory nor intending to limit in any measure the scope of the appended claims or their equivalents, it is presently believed that heavier phosphite esters (e.g., one or more of the phosphites described above) will likely be stable under typical distillation conditions such as may be encountered in refining natural oils and, therefore, that these materials are not likely to contaminate distallates. This represents a significant advantage over the use of lower molecular weight materials that can decompose and/or co-distill with products under typical refining conditions.

Example 9

Susceptibility of Isomerization Suppression Agent to Transesterification Conditions Five different DOVERPHOS® materials were subjected to transesterification conditions (e.g., methoxide/methanol for one hour at 60° C.) in order to assess their susceptibility to transesterification conditions (e.g., such as might be employed for transesterifying a triacylglyceride fraction to produce one or a plurality of transesterification products, as shown in FIG. 3 and as described above). Two of the five materials cleared up during the reaction (i.e., became monophasic) with DOVERPHOS® 4 apparently having reacted and DOVERPHOS® 253 apparently not having reacted to any significant degree.

Three of the five materials—DOVERPHOS® 53, DOVERPHOS® 6, and DOVERPHOS® 613—did not clear up and remained biphasic. Analysis by GC-MS suggests that a reaction may have occurred although the extent was not quantified. Accordingly, while neither desiring to be bound by any particular theory nor intending to limit in any measure the scope of the appended claims or their equivalents, it is presently believed that in some embodiments, these isomerization suppression agents would emerge in the FAME fraction shown in FIG. 3. Moreover, while neither desiring to be bound by any particular theory nor intending to limit in any measure the scope of the appended claims or their equivalents, it is presently believed that if reaction occurs (such as is apparently the case with DOVERPHOS® 4), some of the reaction products could also end up in the glycerol phase.

Thus, the choice of isomerization suppression agent may be guided by a consideration of the desired ultimate destination for the agent within a particular process scheme. For example, in some embodiments, it is desirable to select an isomerization suppression agent that does not end up contaminating a desired product stream. In some embodiments—particularly though not exclusively those involving metathesis-based methods for refining natural oil feedstocks, as shown in FIG. 3—it is desirable to isolate the olefins formed in the metathesis reaction without contamination from the isomerization suppression agent (e.g., a phosphite ester). In some embodiments, as shown in FIG. 3, subsequent transesterification of the triacylglyceride fraction can provide one or a plurality of transesterification products (e.g., FAMEs and/or other esters) that are substantially devoid of phosphorus contamination as a consequence of the phosphite ester remaining in the distillation bottoms (i.e., not being transesterified) or being hydrolyzed.

TABLE 1

ISOMERIZATION SUPPRESSION RESULTS OF PHOSPHOROUS OXO ACID ESTERS

| Phosphorus Esters | Molar Excess over Catalyst | Isom. (duplicates) | Isom. (Control - non-suppressed run) | Comments |
|---|---|---|---|---|
| DOVERPHOS ® 53 | 10 | 0.9, 1.0 (1 hr) | 30.6 (lowest level of isom) | Pretreatment was for one hour at 60° C. |
| DOVERPHOS ® 4 (trisnonylphenyl phosphite, TNPP) | 10 | 1.1, 0.8 | 22.7, 28.3 | As above |
| Galata TNPP | 10 | 0.3, 0.5 | 6.5, 8.5 | Change in TNPP provider and in the cross-metathesized oil used |
| Galata TNPP | 3 | 0.7 to 3.5 (four runs) | 15.9, 14.9 | Shear mixing employed |
| Trimethyl Phosphite | 100 | 0.4 | 25.9 | Direct addition to SSI |
| Diethyl Phosphite | 100 | 0.5 | 22.4 | Direct addition to SSI |
| DEQUEST ® 539 | 100 | 2.0, 2.5 | 40.3 | Mixture of phosphonate esters |

The entire contents of each of U.S. Pat. No. 6,215,019 B1, United States Patent Application Publication No. 2011/0113679 A1, International Patent Publication No. WO 01/36368, and Chapter 11 of *Advanced Inorganic Chemistry, Fifth Edition* (pages 382-443) cited above are hereby incorporated herein by reference, except that in the event of any inconsistent disclosure or definition from the present specification, the disclosure or definition herein shall be deemed to prevail.

The foregoing detailed description and accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents It is to be understood that the elements and features recited in the appended claims may be combined in different ways to produce new claims that likewise fall within the scope of the present invention. Thus, whereas the dependent claims appended below may depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A method for suppressing isomerization of an olefin metathesis product, the method comprising:
   providing a mixture comprising an olefin metathesis product and residual metathesis catalyst; and
   adding a isomerization suppression agent to the mixture to passivate at least a portion of the residual metathesis catalyst;
   wherein the isomerization suppression agent comprises a compound selected from the group consisting of: $R^1HP(O)OR^2$, $R^3R^4P(O)OR^5$, and combinations thereof, wherein $R^1$, $R^2$, $R^3$, $R^4$, and $R^5$ are alike or different and are each independently selected from the group consisting of substituted or unsubstituted $C_1$-$C_{100}$ alkyl, substituted or unsubstituted aryl, and combinations thereof, wherein $R^1$ and $R^2$ may optionally combine to form a bidentate substituent to the phosphorus atom, and wherein any two or three of $R^3$, $R^4$, and $R^5$ may optionally combine to form a bidentate or tridentate substituent to the phosphorus atom.

2. The method of claim 1, wherein the olefin metathesis product comprises a terminal carbon-carbon double bond.

3. The method of claim 1, wherein the olefin metathesis product comprises an internal carbon-carbon double bond.

4. The method of claim 1, wherein the olefin metathesis product comprises a carboxylic acid moiety or a derivative thereof.

5. The method of claim 4, wherein the olefin metathesis product comprises a carboxylic ester moiety.

6. The method of claim 4, wherein the olefin metathesis product is selected from the group consisting of 9-decenoic acid, an ester of 9-decenoic acid, 9-undecenoic acid, an ester of 9-undecenoic acid, an ester of 9-dodecenoic acid, an ester of 9-dodecenoic acid, 1-decene, 2-dodecene, 3-dodecene, and combinations thereof.

7. The method of claim 1, wherein the olefin metathesis product is derived from a natural oil.

8. The method of claim 7, wherein the natural oil is selected from the group consisting of canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, camelina oil, pennycress oil, hemp oil, algal oil, castor oil, lard, tallow, poultry fat, yellow grease, fish oil, tall oils, and combinations thereof.

9. The method of claim 1, wherein the olefin metathesis product is formed from a metathesis reaction comprising self-metathesis of a natural oil.

10. The method of claim 1, wherein the olefin metathesis product is formed from a metathesis reaction comprising cross-metathesis between a natural oil and a low molecular weight olefin.

11. The method of claim 1, wherein the residual metathesis catalyst comprises a transition metal selected from the group consisting of ruthenium, rhenium, tantalum, nickel, tungsten, molybdenum, and combinations thereof.

12. The method of claim 11, wherein the residual metathesis catalyst comprises ruthenium.

* * * * *